US010806913B2

(12) United States Patent
Ross

(10) Patent No.: US 10,806,913 B2
(45) Date of Patent: *Oct. 20, 2020

(54) METHODS FOR BETTER DELIVERY OF ACTIVE AGENTS TO TUMORS

(71) Applicant: Sorrento Therapeutics, Inc., San Diego, CA (US)

(72) Inventor: Russell Frederick Ross, Jacksonville Beach, FL (US)

(73) Assignee: SORRENTO THERAPEUTICS, INC., San Diego, CA (US)

(*) Notice: Subject to any disclaimer, the term of this patent is extended or adjusted under 35 U.S.C. 154(b) by 79 days.

This patent is subject to a terminal disclaimer.

(21) Appl. No.: 15/744,346

(22) PCT Filed: Jul. 22, 2016

(86) PCT No.: PCT/US2016/043623
§ 371 (c)(1),
(2) Date: Jan. 12, 2018

(87) PCT Pub. No.: WO2017/019526
PCT Pub. Date: Feb. 2, 2017

(65) Prior Publication Data
US 2018/0193624 A1    Jul. 12, 2018

Related U.S. Application Data

(60) Provisional application No. 62/196,570, filed on Jul. 24, 2015, provisional application No. 62/196,578, filed on Jul. 24, 2015.

(51) Int. Cl.
A61M 37/00    (2006.01)
A61K 9/00    (2006.01)

(52) U.S. Cl.
CPC ....... *A61M 37/0015* (2013.01); *A61K 9/0014* (2013.01); *A61K 9/0021* (2013.01);
(Continued)

(58) Field of Classification Search
CPC .. A61M 2037/0007; A61M 2037/0023; A61M 2037/003; A61M 2037/0038;
(Continued)

(56) References Cited

U.S. PATENT DOCUMENTS 5,800,420 A    9/1998 Gross et al.
2002/0037311 A1    3/2002 Fikstad et al.
(Continued)

FOREIGN PATENT DOCUMENTS

RU    2328276 C2    7/2008
WO    2006031856 A2    3/2006
(Continued)

OTHER PUBLICATIONS

International Search Report and Written Opinion issued in PCT/US2016/43623 dated Nov. 2, 2016.
(Continued)

*Primary Examiner* — Quynh-Nhu H. Vu
(74) *Attorney, Agent, or Firm* — Armstrong Teasdale LLP

(57) ABSTRACT

The present invention concerns delivery of agents through the skin. Methods for delivering agents such as bioactive agents are contemplated by the present invention. Specifically, methods for the targeted delivery of agents to one or more areas of the epidermis and thereby, to one or more cancer tumors are described.

14 Claims, 14 Drawing Sheets

(52) U.S. Cl.
CPC ............... *A61M 2037/0007* (2013.01); *A61M 2037/0023* (2013.01); *A61M 2037/0038* (2013.01); *A61M 2037/0061* (2013.01)

(58) Field of Classification Search
CPC ...... A61M 2037/0061; A61M 37/0015; A61K 9/0014; A61K 9/0021
See application file for complete search history.

(56) References Cited

U.S. PATENT DOCUMENTS

| | | | |
|---|---|---|---|
| 2005/0163711 A1* | 7/2005 | Nycz | A61P 31/00 424/9.1 |
| 2005/0180952 A1 | 8/2005 | Pettis et al. | |
| 2007/0088414 A1 | 4/2007 | Campbell | |
| 2011/0270221 A1 | 11/2011 | Ross | |
| 2012/0187814 A1 | 7/2012 | Fryling | |
| 2012/0195957 A1 | 8/2012 | Sachdeva | |
| 2012/0245445 A1* | 9/2012 | Black | A61B 10/0045 600/365 |
| 2013/0144217 A1 | 6/2013 | Ross | |
| 2013/0144257 A1 | 6/2013 | Ross | |
| 2013/0150822 A1 | 6/2013 | Ross | |
| 2013/0158505 A1 | 6/2013 | Ross | |
| 2013/0165861 A1 | 6/2013 | Ross | |
| 2014/0248211 A1 | 9/2014 | Bender | |
| 2014/0343532 A1 | 11/2014 | Ross | |
| 2015/0157809 A1 | 6/2015 | Park et al. | |
| 2015/0360018 A1 | 12/2015 | Baker et al. | |
| 2015/0367117 A1 | 12/2015 | Ross et al. | |
| 2016/0106965 A1 | 4/2016 | Baker et al. | |
| 2018/0193625 A1* | 7/2018 | Ross | A61M 37/0015 |

FOREIGN PATENT DOCUMENTS

| | | |
|---|---|---|
| WO | 2011139713 A2 | 11/2011 |
| WO | 2013059343 A1 | 4/2013 |
| WO | 2013061208 A1 | 5/2013 |

OTHER PUBLICATIONS

Moghimim et al., Pharmacological Reviews, 2(53), 283-318 (2001).
Xie et al., Expert Opin Drug De/iv., 6(8), 785-792 (2009).
Zhang and Wei-Yue., Cancer Biol Med., (11), 247-254 (2014).
William D. James, Timothy Berger, and Dirk Elston., Clinical Dermatology (11th ed. 2011).
Physiology, Biochemistry, and Molecular Biology of the Skin, Second Edition, (L.A. Goldsmith, Ed., 2nd ed. Oxford University Press, New York, 1991).
Sennhen, et al., Skin Pharmacol., 6(2), 152-160 (1993).
Gotter, et al., Skin Pharmacol. Physiol., 21, 156-165 (2008).
Advanced Drug Delivery Reviews, 50, 143-156 (2001).
Mogensen, et al., Semin. Cutan. Med. Surg., 28, 196-202 (2009).
William N. Charman and Valentino J. Stella, Lymphatic Transport of Drugs (1992).
Wiig and Swartz., Phsiol. Rev., 1005-1060, (2012).
Ding and Wu., Theranostics, 2(11), 1040-1053 (2012).
Bolch, et al., J. Nucl. Med., 50(3), 477 (2009).
Sevick-Muraca, et al., J. Clin Invest., 124(3), 905-914 (2014).
Remington: The Science and Practice of Pharmacy (*Lloyd V. Allen Jr.* ed., 22nd ed. 2012).
Dynamic Contrast-Enhanced 20 Magnetic Resonance Imaging in Oncology (Jackson et al. eds., 2013).
Gillies and Morse., Annu. Rev. Biomed Eng., 7, 287-326 (2005).
Prasunitz and Langer, Nature Biotechnol, 26(11), 1261-1268 (2008).
Methods Mo/ Biol., (763) 73-81 (2012).
J. Pharmacobio-Dyn., 8, 206-210 (1985).
Pharmaceutical Research, vol. 5, No. 8, 1988.
FDA Guidelines for Bioavailabilty Studies, U.S. Department of Health and Human Services, Aug. 2000.
Matsumura, Yasuhiro, Cancer Research, vol. 45, 6387-6392, Dec. 1986.
Extended European Search Report regarding European Patent Application Serial No. 16831139.7 dated Mar. 18, 2019, pp. 1-13.
English translation of Official Action regarding Russian Patent Application Serial No. 2018104102, dated Oct. 22, 2019, pp. 1-8.
Translation of JPO Office Action for Japanese Patent Application No. 2018-500406 received May 20, 2020; 10 pp.

* cited by examiner

METHODS FOR BETTER DELIVERY OF ACTIVE AGENTS TO TUMORS

FIGURE I

FIGURE 5
Animal ID: 7664 (device on right hip)
Penetration: Needle depth analysis
| Statistics for Average Depth with Zero's | |
|---|---|
| Average | 32.3 |
| Standard Deviation | 34.635 |
| Skew | 0.374 |
| Kurtosis | 1.7340 |
Maximum depth:200um
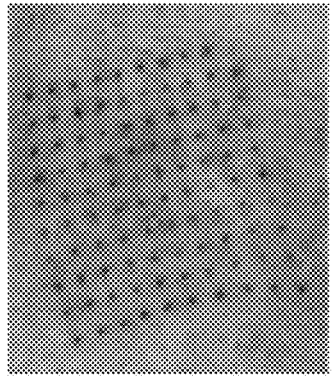
Zero depth (prior to slicing on cryostat) KC26Rg_011
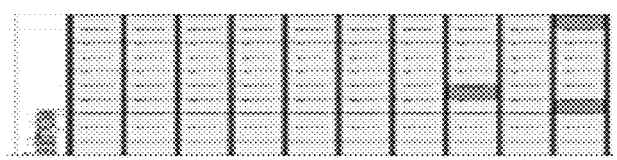
Measured depth (um)
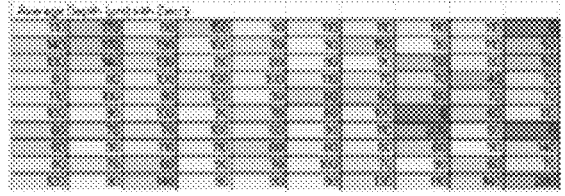
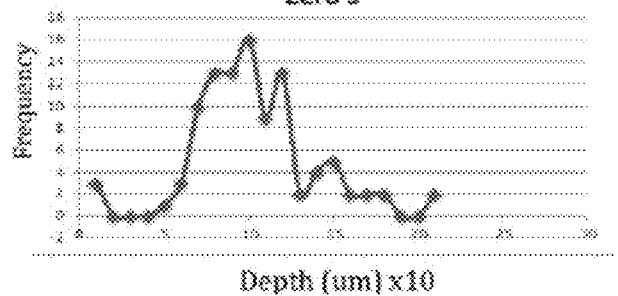
Depth (um) x10

METHODS FOR BETTER DELIVERY OF ACTIVE AGENTS TO TUMORS

CROSS REFERENCE TO RELATED APPLICATIONS

This application is a United States National Phase Application of PCT/US2016/43623, filed Jul. 22, 2016, which claims priority to U.S. Provisional Patent Applications 62/196,570 and 62/196,578 both having a filing date of Jul. 24, 2015 all of which are incorporated by reference in their entirety.

TECHNICAL FIELD

The present invention concerns delivery of agents through the skin. Methods for deliver-ing agents such as bioactive agents are contemplated by the present invention. Specifically, methods for the targeted delivery of agents to one or more areas of the epidermis and thereby, to one or more cancer tumors are described.

BACKGROUND

Cancer is the second leading cause of mortality in the United States, superseded only by heart disease with solid tumors accounting for more than 85% of cancer mortalities. Currently, the standard of care treatment for patients presenting with solid tumors is invasive surgery followed by adjuvant chemotherapy and/or radiotherapy. While this strategy has been successfully employed at times, it is accompanied with cytotoxicity to normal cells and tissues, in addition to the development of multidrug resistance (MDR).

Targeted cancer therapies offer the potential to improve the treatment of solid tumors. The thought bas been by targeting therapeutic agents to solid tumors, cytotoxicity to normal cells and tissues may be minimized and potentially limit the emergence of drug resistance.

Current targeted delivery approaches that have been explored include using nanoparticles (NPs), such as micelles, liposomes, and dendrimers administered intravenously (i.v.) carrying a drug payload for the targeted delivery of therapeutic agents to solid tumors. Currently, systemic delivery of therapeutic agents via nanoparticles to solid tumors is a three step process: (1) systemic delivery of the therapeutic agent to different regions of the tumor; (2) transport of the therapeutic agent across the vessel wall into the solid tumor (extravasation); and (3) passage of the therapeutic agent from the tumor tissue adjacent to the vasculature to the tumor cells via diffusion through the interstitial space.

Nanoparticles injected i.v. must remain in the systemic circulation long enough for a portion to extravasate and accumulate within a solid tumor tissue. Nanoparticles are capable of accumulating in solid tumors due to the enhanced permeability and retention (EPR) effect Masumura, et al., *Cancer Research*, (46), 6387-6392 (1986). The EPR effect is a consequence of the abnormal vasculature frequently associated with solid tumors. The vasculature of tumors is typically characterized by blood vessels containing poorly-aligned defective endothelial cells with wide fenestrations often lacking smooth muscle and a basement membrane. However, the extent of the presence of intra tumor vasculature, high tumor interstitial tissue fluid pressure, and tumor vasculature composition heterogeneity make consistent delivery using these types of approaches problematic.

Thus, despite the presence of the EPR effect, these prior approaches are severely limited as the majority of nanoparticles (>95%) accumulate in other organs and tissues (e.g., the liver, spleen, and lungs). Further accounting for this effect, is evidence suggesting that larger nanoparticles more effectively accumulate within tumors, but are subject to higher rates of clearance from the blood circulation see, for example, Moghimim et al., *Pharmacological Reviews*, 2(53), 283-318 (2001).

Additional approaches have been to utilize specific ligand/receptor interactions for an active targeting of drugs or drug carrier nanoparticles or modifications to increase plasma half-life to increase chances of the EPR effect. For example, PEGylated drug carriers have been shown to have increased systemic circulation retention. Modest increases in tumor delivery were observed, but still >90% of the delivered dose was systemically cleared within a few hours. Active targeting approaches may provide increased drug release selectivity but are similarly limited as they also rely on initial i.v. administration and subsequent extravasation of the drug or drug carrier, which can similarly lead to accumulation in distant tissues far from the tumor to be treated.

For example, two nanoparticle drug formulations have been approved by the FDA, DOXIL® (a 100 nm PEGylated liposomal form of doxorubicin) and ABRAXANE® (an 130 nm albumin-bound paclitaxel nanoparticle). While these formulations have exhibited some improved pharmacokinetic properties and reduced adverse effects, they provided only modest survival benefits. Thus, the limited efficacy of these existing nanoparticle formulations likely stems from their inability to effectively deliver the therapeutic agents to the solid tumor.

Therefore new methods for delivering increased concentrations of agents to solid tumors are greatly needed.

SUMMARY

One embodiment described herein is a method of delivering one or more agents to one or more susceptible tumors of a subject, the method comprising: (a) contacting one or more layers of epidermis with one or more reversible permeability enhancers, wherein the one or more reversible permeability enhancers induces a reversible increase in the permeability of one or more barrier cells of the epidermis to at least the one or more agents; (b) administering a total liquid dosage in between 2 and 50,000 sub-doses of the one or more agents at a controlled administration flow rate, wherein each sub-dose of the one or more agents is independently administered to a plurality of independent depths within the epidermis prior to any subsequent diffusion or movement of the one or more agents within the epidermis; and wherein following administration, the permeability of the one or more barrier cells returns to a normal state prior to the contacting of the epidermis with the one or more permeability enhancers.

Another embodiment described herein is a method of treating a subject with a disease comprising one or more tumors by administering one or more bioactive agents to the one or more tumors comprising: (a) applying one or more delivery devices having between 2 and 50,000 delivery structures to one or more sites of skin comprising blood vasculature and lymphatic vasculature, wherein the delivery device contacts one or more layers of epidermis with one or more reversible permeability enhancers that induces a reversible increase in the permeability of one or more barrier cells of the epidermis to at least the one or more bioactive agents; (b) administering a total liquid dosage in between 2 and 50,000 sub-doses of the one or more bioactive agents at a controlled administration flow rate through the delivery device wherein each sub-dose of the one or more bioactive agents is independently administered to a plurality of independent depths within the epidermis prior to any subsequent diffusion or movement of the one or more bioactive agents within the epidermis; wherein following the administering step, the one or more bioactive agents moves or diffuses deeper through the epidermis through a basal layer of the epidermis and into at least a portion of underlying viable dermis to achieve an uptake of a portion of the one or more bioactive agents by one or more susceptible blood capillary plexus or lymphatic capillary plexus; wherein after administration and uptake, the one or more bioactive agents circulates through the blood vasculature or lymphatic vasculature to one or more tumors; and wherein a greater concentration of the one or more bioactive agents is delivered to the one or more tumors compared to intravenous, intradermal, or subcutaneous delivery of the identical one or more bioactive agents.

In some aspects of the embodiments described herein, the epidermis comprises both nonviable epidermis and viable epidermis.

In some aspects of the embodiments described herein, the plurality of independent depths has a combined average depth of administration within the epidermis, wherein each independently administered sub-dose is at a depth within the epidermis that is a deeper depth, a shallower depth, or a same depth.

In some aspects of the embodiments described herein, the total liquid dosage of the one or more agents administered to plurality of depths within the epidermis comprises administration to a depth within at least a portion of non-viable epidermis and/or at least a portion of viable epidermis.

In some aspects of the embodiments described herein, the plurality of depths within the epidermis is from about 1 μm to about 500 μm beyond a most superficial surface layer of the epidermis of the subject.

In some aspects of the embodiments described herein, the total liquid dosage of the one or more agents is administered to a plurality of depths within the epidermis consisting only of one or more viable epidermal layers and not a non-viable epidermal layer.

In some aspects of the embodiments described herein, the plurality of depths within the viable epidermis is from about 1 μm to about 250 μm beyond the deepest non-viable epidermal layer but still within the viable epidermis.

In some aspects of the embodiments described herein, the average of the independent plurality of depths exhibits a combined average sub-dose delivery depth within the epidermis of about 70 μm to about 175 μm beyond the most superficial surface layer of the epidermis.

In some aspects of the embodiments described herein, a frequency of each of the independent sub-dose administration depth within the viable and/or non-viable epidermis exhibits a Gaussian distribution of depths.

In some aspects of the embodiments described herein, the one or more agents are administered by applying one or more delivery devices to one or more sites of the skin.

In some aspects of the embodiments described herein, the delivery device comprises an array comprising between 2 and 50,000 delivery structures in fluid communication with one or more agents in a liquid carrier vehicle, wherein the delivery device comprises a means for controlling the administration flow rate; wherein the delivery structures comprise a means for penetrating at least a most superficial layer of the epidermis; and wherein the one or more agents in a liquid carrier vehicle is delivered by the delivery structures to the plurality of depths within the viable epidermis of a subject, thereby administering between 2 and 50,000 sub-doses of the one or more agents.

In some aspects of the embodiments described herein, the delivery structures comprise a standard or non-standard geometric shape.

In some aspects of the embodiments described herein, the delivery structures comprise needles.

In some aspects of the embodiments described herein, the one or more agents is administered at a controlled administration flow rate of about 0.01 μl/hr to about 100 μl/hr per delivery structure.

In some aspects of the embodiments described herein, the overall controlled administration flow rate of the one or more agents to the plurality of depths within the epidermis is from about 0.02 μl/hr/cm$^2$ to about 50,000 μl/hr/cm$^2$ based on the total surface area of a delivery device that is in contact with the skin of the subject.

In some aspects of the embodiments described herein, the one or more agents is delivered to a tissue volume of the epidermis encompassing the one or more agents prior to any subsequent diffusion or movement of the one or more agents within the epidermis of about 0.7 mm$^3$ to about 2,500 mm$^3$.

In some aspects of the embodiments described herein, the one or more agents are continuously administered to a subject for a time period of about 0.1 hours to about 96 hours.

In some aspects of the embodiments described herein, the one or more permeability enhancers are one or more chemical, physical, or electrical permeability enhancers.

In some aspects of the embodiments described herein, the physical permeability enhancers comprise a nanostructured or nanotopography surface.

In some aspects of the embodiments described herein, the nanotopograhy surface is fabricated on the surface of the delivery structures as described herein.

In some aspects of the embodiments described herein, the administered one or more agents to the plurality of depths within the skin moves or diffuses deeper through the epidermis through a basal layer of the epidermis and into at least a portion of underlying viable dermis.

In some aspects of the embodiments described herein, the administration of one or more agents achieves a dermal interstitial fluid pressure in the underlying dermis of about 1 mmHg to about 15 mmHg.

In some aspects of the embodiments described herein, the one or more agents is absorbed by one or more tissues comprising one or more susceptible lymphatic capillary plexus or one or more blood capillary plexus following delivery to the epidermis.

In some aspects of the embodiments described herein, the one or more agents circulate through the one or more blood capillary plexus and into or within proximity to one or more susceptible tumors.

In some aspects of the embodiments described herein, the one or more agents circulate through the one or more lymphatic capillary plexus and into or within proximity to one or more susceptible tumors.

In some aspects of the embodiments described herein, the concentration of one or more agents within one or more susceptible tumors is about 1.25 fold to about 50 fold more than intravenous, intradermal, or subcutaneous delivery of the identical one or more agents.

In some aspects of the embodiments described herein, a blood serum absorption rate of the one or more agents is equivalent to intradermal delivery and subcutaneous delivery of the identical one or more agents.

In some aspects of the embodiments described herein, the one or more agents comprise a bioactive agent.

In some aspects of the embodiments described herein, the bioactive agent is useful for treating, retarding the progression of, delaying the onset of, prophylaxis of, amelioration of, or reducing the symptoms of a disease in a patient in need of treatment thereof.

BRIEF DESCRIPTION OF THE DRAWINGS

FIG. 5. Schematic of the delivery methods to the skin illustrating average depth of delivery.

DETAILED DESCRIPTION

Figure 1:
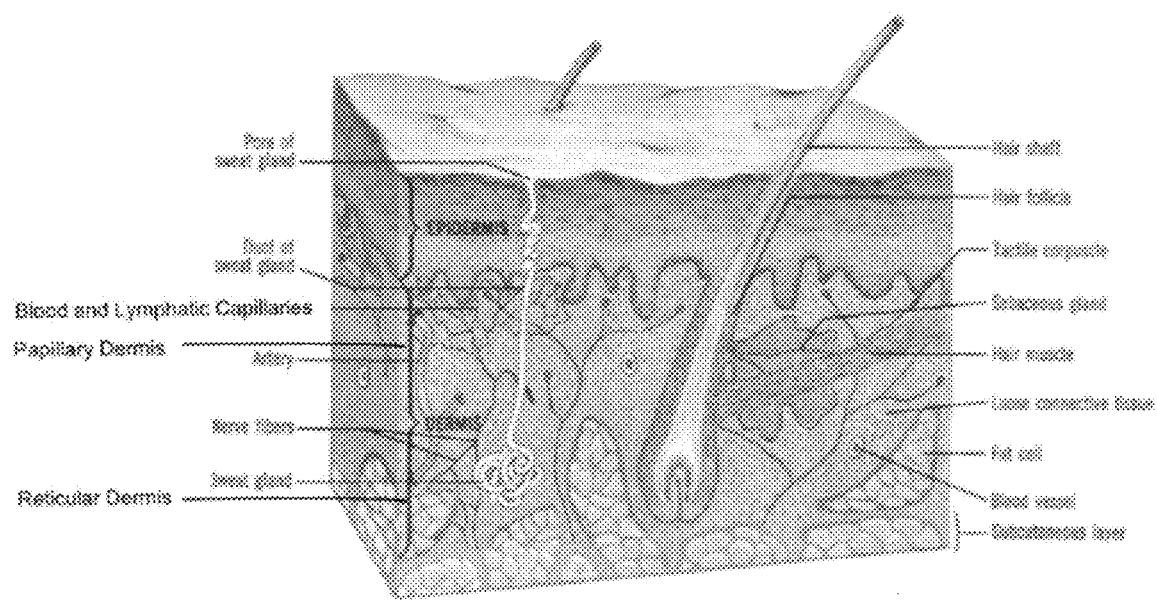
FIG. 1. Schematic of the skin including the epidermis and dermis illustrating the various tissues of the skin.

There is a need for methods of controlled delivery of agents (e.g., bioactive agents) to solid cancer tumors of subjects. Therefore, described herein are methods for the controlled delivery of one or more agents to the skin followed by the uptake of the one or more agents by tumors. In some embodiments described herein the uptake of the one or more agents by one or more tumors is facilitated by primary absorption of the lymphatic tissues followed by delivery through the lymphatic vasculature to one or more susceptible tumors.

The term "viable skin" as used herein refers to an area of the skin immediately below the stratum corneum layer of the epidermis including the dermis, but above the subcutaneous tissue layers. This term encompasses both the viable epidermis and the viable dermis. The actual depth of the viable skin will vary depending on location of the skin, age, and physiology of a given subject. The term viable skin further specifies that this portion of the skin comprises nucleated living cells, often mitotic. In some aspects described herein, the viable skin also comprises at least one or more lymphatic capillary plexus and/or one or more blood capillary plexus.

The term "viable dermis" as used herein refers to an area of the skin immediately below the basal layer of the epidermis but above the subcutaneous tissue layer. The viable dermis comprises both the papillary and reticular dermal layers of the dermis, further comprising, for example, blood capillaries and lymphatic capillaries amongst other tissue types.

The term "viable epidermis" as used herein refers to an area of the skin immediately below the stratum corneum. The viable epidermis comprises the basal layer or stratum germinativum, the squamous cell layer or the stratum spinosum and the granular cell layer or the stratum granulosum.

The term "agent" as used herein refers to a compound, substance, composition, or molecule to be delivered. Exemplary and non-limiting examples include bioactive agents, nucleic acids (e.g., micro RNAs), dyes (e.g., contrast agents and fluorescent reporters), vaccines and the like.

The term "bioactive agent," as used herein refers to any biocompatible agent, which elicits a cellular response. The term bioactive agent comprises any drug, active ingredient, active drug substance, or vaccine. For example, a bioactive agent described in the embodiments herein, may comprise drugs, such as small molecule drugs, bio-similar drugs, biologics, etc., nanoparticles, lipids, liposomes, proteins (e.g., recombinant proteins, antibodies, etc.), and the like.

The terms "drug", "active ingredient," "active drug substance," or "active pharmaceutical agent" as used herein refer to an active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" denote any form of the active ingredient formulation that contains an amount sufficient to produce a therapeutic effect with a single administration.

The term "titration" as used herein refers to the incremental increase in drug dosage or administration rate to a level that provides the optimal therapeutic effect.

The term "controlled delivery" as used herein refers to an administration method that results in the controllable delivery of one or more agents over a desired period of time. As used herein, it encompasses the terms "modified delivery," "sustained delivery," "extended delivery," and "delayed delivery." In some aspects described herein, the methods for controlled delivery result in the delivery of one or more agents or active drug substances to achieve a therapeutic threshold for a maximal length of time.

The term "delayed delivery" as used herein refers to the delivery of one or more agents according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours;

about 14 hours; about 16 hours; about 18 hours; about 20 hours about 24 hours; or even longer.

The term "modified delivery" as used herein refers to the delivery of one or more agents at a slower rate than does immediate delivery formulation under physiological conditions or in an in vitro test.

The term "sustained delivery" as used herein refers to the delivery of one or more agents over an extended period of time, for example minutes, hours, or days, such that less than all the active ingredient is released initially. A sustained release rate may provide, for example, the delivery of a certain specified amount of one or more agents or active drug substances over a certain period, under physiological conditions or in an in vitro test.

The term "extended delivery" as used herein refers to the delivery of one or more agents over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours, about 24 hours, about 48 hours, about 72 hours; or even longer.

The term "initial delivery" or "initially delivered" refers to a tissue location at which an agent first comes into contact. In some aspects described herein, initial delivery may refer to a location within the skin (e.g., non-viable epidermis, viable epidermis, or viable dermis) in which one or more agents first contacts after being delivered through a delivery device or one or more delivery structures of a delivery device.

As used herein, "conventional delivery" means any method prior to the present invention that is used in the art for delivering one or more materials having biological kinetics or activity similar to intravenous (i.v.), iontophoretic, subcutaneous (s.c.), intramuscular (i.m.), or intradermal (i.d.) injections, or topical formulations. Exemplary methods include subcutaneous, iontophoretic, and intradermal delivery methods, such as those described in U.S. Pat. No. 5,800,420, US 20050180952, Xie et al., *Expert Opin Drug Deliv.*, 6(8), 785-792 (2009) and Zhang and Wei-Yue., *Cancer Biol Med.*, (11), 247-254 (2014), each of which is incorporated by reference herein with regard to a general description of conventional delivery methods.

The term "targeted drug delivery" refers to the predominant location, wherein a drug accumulates. This term is separate and distinct from commonly used terminology, such as "targeted therapy," which more specifically refers to a specific interaction with a cell or tissue type (e.g., a ligand/receptor interaction).

The term "BCS Class I, II, II, or IV" refers to whether a compound or active drug substance has high or low permeability and high or low solubility (e.g., poorly soluble). BCS Class I drugs have high permeability and high solubility; BCS Class II drugs have high permeability and low solubility, BCS Class III drugs have low permeability and high solubility, and BCS Class IV drugs have low permeability and low solubility. An immediate release drug substance is considered highly soluble when the highest dose strength is soluble in 250 mLs or less of aqueous media over the pH range of 1 to 7.5 at 37±1° C. A sufficient number of pH conditions should be evaluated to accurately define the pH-solubility profile. In the absence of evidence suggesting instability in the gastrointestinal tract, an immediate release drug substance is considered to be highly permeable when the extent of absorption in humans is determined to be 90% or more of an administered dose based on the mass balance determination or in comparison to an intravenous reference dose. Permeability can be determined using mass balance, absolute bioavailability, or intestinal perfusion approaches. When a single method fails to conclusively demonstrate the permeability classification, two different methods may be advisable. A drug product is considered rapidly dissolving when no less than 85% of the labeled amount of the drug substance dissolves within 30 minutes, using USP Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes. See, FDA Guidance for Industry: Waiver of In Vivo Bioavailability and Bioequivalence Studies for Immediate-Release Solid Oral Dosage Forms Based on a Biopharmaceutics Classification System. (August 2000), which is incorporated by reference herein for such teachings.

As used herein, "bioavailability", means the total amount of a given dosage of the administered agent that reaches the blood compartment. This is generally measured as the area under the curve in a plot of concentration vs. time.

As used herein "tissue" refers to a group or layer of cells that together perform a function including but not limited to, skin tissue, lymphatic tissue (e.g., lymph nodes), mucosal tissue, reproductive tissue, cervical tissue, vaginal tissue and any part of the body that consists of different types of tissue and that performs a particular function, i.e., an organ, including but not limited to lung, spleen, colon, thymus. As used herein, tissue includes any tissue that interacts with or is accessible to the environment, e.g., skin or mucosal tissue.

As used herein, "tissue-bioavailability" means the amount of an agent that is biologically available in vivo in a particular tissue. These amounts are commonly measured as activities that may relate to binding, labeling, detection, transport, stability, biological effect, or other measurable properties useful for diagnosis and/or therapy. In addition, it is understood that the definition of "tissue-bioavailability" also includes the amount of an agent available for use in a particular tissue. "Tissue-bioavailability" includes the total amount of the agent accumulated in a particular tissue, the amount of the agent presented to the particular tissue, the amount of the agent accumulated per mass/volume of particular tissue, and amount of the agent accumulated per unit time in a particular mass/volume of the particular tissue. Tissue bioavailability includes the amount of an agent that is available in vivo in a particular tissue or a collection of tissues such as those that make up the vasculature and/or various organs of the body e.g., a part of the body that consists of different types of tissue and that performs a particular function.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0\to\tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0\to12}$ as used herein refers to the area under the concentration versus time curve from 0 to 12 hours.

The term "$AUC_{0\to\infty}$" as used herein refers to the area under the blood (plasma, serum, or whole blood) concentration versus time curve from time 0 hours to infinity, and is expressed in units of h mg/L or h·ng/mL, as applicable.

The term "$AUC_{overall}$" as used herein refers to the combined area under the blood (plasma, serum, or whole blood) concentration versus time curve, and is expressed in units of h mg/L (or h ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely. In some aspects, substantially means 90% to 99% or more in the various embodiments described herein, including each integer within the specified range.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, the terms "disorder" and "disease" are used interchangeably to refer to a condition in a subject. Diseases include to any interruption, cessation, or disorder of body functions, systems or organs.

As used herein, the terms "treat," "treating" and "treatment" refer to the eradication, reduction or amelioration of symptoms of a disease or disorder. In some embodiments, treatment refers to the eradication, removal, modification, or control of primary, regional, or metastatic cancer tissue that result from the administration of one or more therapeutic agents. In certain embodiments, such terms refer to the minimizing or delaying the spread of cancer resulting from the administration of one or more therapeutic agents to a subject with such a disease.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the recurrence or onset of one or more symptoms of a disorder in a subject resulting from the administration of a prophylactic or therapeutic agent As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art, see, e.g., the Physicians' Desk Reference ($69^{th}$ ed., 2015), which is incorporated herein by reference in its entirety.

As used herein, the phrase "delivery to a susceptible tissue" or a "viable tissue" refers to the delivery of one or more agents to a living tissue or tissue structure, for example the skin, spleen, thymus, lung, vasculature, lymphatic vasculature, lymph nodes, heart and brain, etc. In some embodiments described herein, the methods, compositions, and devices further described herein may modulate the structure of a living tissue or tissue structure to facilitate the absorption of one or more agents. In some aspects, the living tissue or tissue structure includes the skin and individual viable cells that comprise the skin. In some aspects, described herein, the methods of delivery induce a particular cell or tissue (e.g., the viable skin) to be susceptible to delivering one or more agents to that specific tissue. In some aspects described herein, the living tissue or tissue structure comprises one or more layers of the viable skin such as the viable layers of the epidermis and the underlying dermis. In some aspects described herein, the living tissue or tissue structure comprises lymphatic capillaries, e.g., delivery to a susceptible lymphatic capillary plexus.

Described herein are methods and devices for the initial delivery of agents to the skin, and subsequently to a susceptible tumor. In certain embodiments described herein are methods for delivering agents to the lymphatic vasculature and a susceptible tumor.

In some embodiments described herein are methods for delivering one or more agents to the skin. In some aspects, the one or more agents are delivered to at least a portion or area of the viable skin or non-viable skin. In some aspects, the one or more agents are delivered to at least a portion or area of the viable epidermis. In some aspects, the one or more agents are delivered to at least a portion or area of the non-viable epidermis. As further described herein, the one or more agents are able to pass through the viable epidermis and enter the dermis, thereby coming into proximity with one or more blood or lymphatic capillaries. In some embodiments described herein, delivery of one or more agents to the skin results in the uptake of the one or more agents by a susceptible tumor. The delivery to tumors may be due to absorption by a lymphatic capillary or a blood capillary or both as further described herein.

Delivery to the skin presents several difficulties based upon the barrier providing function of the skin. Anatomically, the skin is broadly made up of two major tissue layers, an outer epidermis and an underlying dermis, which together constitute the skin. The broader integumentary system comprises the skin, hair, nails, exocrine glands, and the subcutaneous tissues. Many transdermal or microneedle approaches for delivery to the skin and through the epidermis and into the viable dermis are unsuccessful because of this barrier function resulting in the delivered materials being retained within one or more layers of the epidermis.

The epidermis is subdivided into four principle layers or strata. In order from bottom to top is the basement membrane, the basal layer or stratum germinativum, the squamous cell layer or the stratum spinosum, the granular cell layer or the stratum granulosum, and the cornified layer or the stratum corneum. Of these three layers, the lower three layers (i.e., stratum germinativum, stratum spinosum, and stratum granulosum) constitute the living layers of the epidermis.

These living layers of the epidermis are important for the barrier function of the skin, which relies on the self-renewal and differentiation of the basally located stem cells to regenerate the upper layers of the skin and provide enucleated cells for the barrier layer or the stratum corneum. The barrier function of the epidermis is largely due to the presence of tight junctions which prevent the passage of macromolecules (e.g., proteins), microorganisms, and other potentially toxic chemicals. Thus, these tight junctions are barrier structures that include a network of transmembrane proteins embedded in adjacent plasma membranes (e.g., claudins, occludin, and junctional adhesion molecules) as well as multiple plaque proteins (e.g., ZO-1, ZO-2, ZO-3, cingulin, symplekin). Tight junctions are found in nearly all types of barrier types of tissue including the internal epithelium (e.g., the intestinal epithelium, the blood-brain barrier, blood vessels, lymphatic vessels) as well as throughout the viable epidermis of the skin.

The thickness of the skin is varied depending on location and age. For example the eye lid has one of the thinnest layers of epidermis at less than about 0.2 mm; the palms of the hands and soles of the feet have some of the thickest layers of epidermis measuring at nearly 1.5 mm. The thickness of the dermis is also varied depending on tissue location with the dermis on the back being 30-40 times thicker than the epidermis see, William D. James, Timothy Berger, and Dirk Elston., Clinical Dermatology ($11^{th}$ ed. 2011), which is incorporated by reference herein in its entirety.

Beneath the epidermis lies the dermis, which contains two layers, an outermost portion referred to as the papillary dermis and a deeper layer referred to as the reticular dermis. The papillary dermis contains vast microcirculatory blood and lymphatic plexuses. In contrast, the reticular dermis is relatively acellular, made up of dense collagenous and elastic connective tissue. Beneath the epidermis and dermis is the subcutaneous tissue, also referred to as the hypodermis, which is composed of connective tissue and fatty tissue. See, Physiology, Biochemistry, and Molecular Biology of the Skin, Second Edition, (L. A. Goldsmith, Ed., $2^{nd}$ ed. Oxford University Press, New York, 1991), which is incorporated by reference herein in its entirety.

Some embodiments described herein are methods for the targeted delivery of one or more agents to one or more tumors. The delivery of one or more agents to one or more tumors is facilitated by the delivery of one or more agents to the skin at a rate and depth as further described herein. The targeted delivery of one or more agents to one or more tumors may be facilitated by delivery to one or more susceptible lymphatic capillary plexus. In some other aspects, the targeted delivery of one or more agents to one or more tumors may be facilitated by the delivery to one or more susceptible blood capillary plexus. In some aspects, the tumor may be a primary tumor or a secondary tumor (e.g., a metastasis of the primary tumor).

In some embodiments described herein, one or more agents are delivered to a position within the skin, wherein after the initial administration, the one or more agents moves or diffuses to a position that is in proximity of the blood vasculature and the lymphatic vasculature. As described herein, this placement within the skin may result in the subsequent delivery of an agent to a lymphatic capillary bed or otherwise known as a lymphatic drainage bed or lymphatic capillary plexus, which physiologically functions to drain interstitial fluid for a given location to the rest of the lymphatic system.

In some embodiments described herein, one or more agents are directly delivered to a position within the epidermis. In some aspects, the one or more agents diffuse, move, flow, or migrate to a position in proximity to the lymphatic vasculature. As described herein, this placement within the epidermis following the methods described herein results in the diffusion or movement of an agent through the epidermis and into the viable epidermis, which allows for direct contact of an agent to the most superficially present lymphatic capillary bed(s) or otherwise known as a lymphatic drainage bed or lymphatic capillary plexus, which physiologically functions to drain interstitial fluid for a given location to the rest of the lymphatic system. In some other aspects, this placement within the skin may result in the localized delivery of an agent to a blood capillary bed. The methods of delivering one or more agents to a lymphatic capillary bed described herein may further result in the delivery of the agent to the first lymph nodes draining the lymphatic capillary bed, also referred to as "primary" lymph nodes. In some aspects, the localized delivery of one or more agents may also result in the delivery of the agent to additional lymph nodes downstream of the primary lymph nodes, also referred to as "secondary" lymph nodes. In some aspects the agent may eventually enter the blood stream and be delivered systemically. In some aspects described herein, the delivery of one or more agents to the skin results in the targeted delivery of the one or more agents to one or more susceptible tumors in a subject.

In some embodiments described herein are methods for delivering one or more agents to a range of depths within the skin. In some aspects, the one or more agents is delivered to the epidermis, which comprises both the non-viable epidermis (e.g., stratum corneum) and the viable epidermis underlying the non-viable epidermis. The depth in the skin may vary depending on location, age and physiology of the skin of a given subject as described herein. The overall depth in the skin of delivery of one or more agents may be described as the distribution of a plurality of depths that the one or more agents may be located following the initial administration of the one or more agents using the methods described herein. The total distribution of depths of delivery of the one or more active agents depends on the rate of administration, volume, and depth within the skin of a delivery structure as described further herein. Therefore, portions of the total delivered agent may be at a more superficial depth or a deeper depth, wherein the total delivered agent has an average delivery depth and standard deviation of a range of delivery depths. Therefore, in some aspects, the delivery of one or more agents to the skin as described herein may follow a simple normal distribution (i.e., a Gaussian distribution) within the skin. In some other aspects, the delivery of one or more agents to the skin may follow a multi-modal distribution of depths within the skin.

As further described herein, the delivery of one or more agents to the epidermis, wherein the administered one or more agents exhibits a distribution of depths within the epidermis provides allows for increased lymphatic uptake of the one or more agents. The delivery methods described herein allow for the previously unrealized aspect of contacting all levels of potential dermal lymphatic capillaries. The methods described herein further comprise reversibly increasing the porosity of the barrier function of the skin to promote the downward (top to bottom) diffusion or movement of an agent throughout all layers of the epidermis and into the viable dermis. In some aspects described herein, delivery to the epidermis yields greater lymphatic uptake compared to alternative parenteral delivery methods, such as direct intradermal delivery techniques, which may miss the initial lymphatic capillaries directly below the basement membrane of the epidermis, resulting in reduced lymphatic uptake. Without being bound by any theory, this may occur because the agent may more freely move downwardly through the reticular dermis and into the subcutaneous tissue. Therefore, by providing methods that allow for the diffusion or movement of an agent through the epidermis at a plurality of flow rates as described herein, the superficial lymphatics and deeper lymphatics within the dermis may be contacted by an agent, which increases the absorption rate or amount of an agent by one or more susceptible lymphatic capillaries.

In some embodiments described herein, at least a portion of or all of one or more agents may be directly delivered or administered to an initial depth in the skin comprising the nonviable epidermis and/or the viable epidermis. In some aspects, a portion of the one or more agents may also be directly delivered to the viable dermis in addition to the epidermis. The range of delivery depth will depend on the disease being treated and the skin physiology of a given subject. This initial depth of delivery may be defined as a location within the skin, wherein an administered agent first comes into contact as described herein. Without being bound by any theory, it is thought that the administered one or more agents may move (e.g., diffuse) from the initial site of delivery (e.g., the non-viable epidermis, the viable epidermis, or the viable dermis) to a deeper position within the viable skin. For example, a portion of or all of an administered agent may be delivered to the non-viable epidermis and then continue to move (e.g., diffuse) into the viable epidermis and past the basal layer of the viable epidermis and enter into the viable dermis. Alternatively, a portion of or all of an administered agent may be delivered to the viable epidermis (i.e., immediately below the stratum corneum) and then continue to move (e.g., diffuse) past the basal layer of the viable epidermis and enter into the viable dermis. Lastly, a portion of or all of an administered agent may be delivered to the viable dermis. The movement of the one or more active agents throughout the skin is multifactorial and, for example, depends on the liquid carrier composition (e.g., viscosity thereof), rate of administration, delivery structures, etc. This movement through the epidermis and into the dermis may be further defined as a transport phenomenon and quantified by mass transfer rate(s) and/or fluid mechanics (e.g., mass flow rate(s)).

Thus, in some embodiments described herein, the one or more agents may be delivered to a depth in the epidermis wherein the one or more agents moves past the basal layer of the viable epidermis and into the viable dermis. In some aspects described herein, the one or more agents are then absorbed by one or more susceptible lymphatic capillary plexus or blood capillaries and then delivered to one or more susceptible tumors.

In some embodiments described herein, the one or more agents may be delivered in a liquid carrier solution. In one aspect, the tonicity of the liquid carrier may be hypertonic to the fluids within the blood capillaries or lymphatic capillaries. In another aspect, the tonicity of a liquid carrier solution may be hypotonic to the fluids within the blood capillaries or lymphatic capillaries. In another aspect, the tonicity of a liquid carrier solution may be isotonic to the fluids within the blood capillaries or lymphatic capillaries. The liquid carrier solution may further comprise at least one or more pharmaceutically acceptable excipients, diluent, cosolvent, particulates, or colloids. Pharmaceutically acceptable excipients for use in liquid carrier solutions is known, see, for example, Pharmaceutics: Basic Principles and Application to Pharmacy Practice (Alekha Dash et al. eds., $1^{st}$ ed. 2013), which is incorporated by reference herein for its teachings thereof.

In some embodiments, the one or more agents may then be directly or indirectly delivered to one or more susceptible tumors by first delivering the one or more agents to a depth in the skin, which results in delivery to a susceptible lymphatic capillary plexus or a blood capillary plexus as described herein. In one aspect, the targeted delivery of one or more agents to one or more susceptible tumors comprises delivery to the epidermis, wherein the one or more agents is absorbed by a susceptible lymphatic capillary plexus prior to being absorbed by one or more susceptible tumors. In another aspect, the targeted delivery of one or more agents to one or more susceptible tumors comprises delivery to the viable epidermis and/or viable dermis, wherein the one or more agents is absorbed by a blood capillary plexus prior to being absorbed by one or more susceptible tumors.

In some embodiments described herein, the distribution of depths in the skin, wherein a portion of the one or more agents is initially delivered, which results in uptake of the one or more agents by one or more susceptible tumors ranges from about 5 µm to about 4,500 µm, including each integer within the specified range. In some aspects, the depth in the skin for initially delivering one or more agents ranges from about 5 µm to about 2,000 µm, including each integer within the specified range. In some aspects, the depth in the skin for initially delivering one or more agents ranges from about 5 µm to about 1,000 µm, including each integer within the specified range. In some aspects, the depth in the skin for initially delivering one or more agents ranges from about 5 µm to about 500 µm, including each integer within the specified range. In some aspects, the depth in the skin for initially delivering one or more agents ranges from about 5 µm to about 250 µm, including each integer within the specified range. In some aspects, the depth in the skin for initially delivering one or more agents ranges from about 5 µm to about 100 µm, including each integer within the specified range. In some aspects, the average depth in the skin for initially delivering one or more agents is about 5 µm, about 10 µm, about 20 µm, about 30 µm, about 40 µm, about 50 µm, about 60 µm, about 70 µm, about 80 µm, about 90 µm, about 100 µm, about 125 µm, about 150 µm, about 175 µm, about 200 µm, about 225 µm, about 250 µm, about 275 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1,000 µm, about 1,100 µm, about 1,200 µm, about 1,300 µm, about 1,400 µm, about 1,500 µm, about 1,600 µm, about 1,700 µm, about 1,800 µm, about 1,900 µm, about 2,000 µm, about 2,250 µm, about 2,500 µm, about 2,750 µm, about 3,000 µm, about 3,250 µm, about 3,500 µm, about 3,750 µm, about 4,000 µm, to about 4,500 µm.

In some embodiments described herein, one or more agents are delivered to the viable skin, wherein the distribution of depths in the viable skin for delivery of the one or more agents is immediately past the stratum corneum of the epidermis but above the subcutaneous tissue, which results in uptake of the one or more agents by one or more susceptible tumors. Whether the agent is within the epidermis or dermis will depend on the thickness of the epidermis, for example, more shallow depths of delivery comprising about 1 µm to about 250 µm past the stratum corneum would be expected to be within the viable epidermis. Depths greater than 400 µm, 500 µm, or 700 µm would likely be expected to be within at least a most superficial portion of the viable dermis (e.g., the papillary dermis). In some aspects, the depth in the viable skin for delivering one or more agents ranges from about 1 µm to about 5,000 µm beyond the stratum corneum, but still within the viable skin above the subcutaneous tissue, including each integer within the specified range. In some aspects, the depth in the viable skin for delivering one or more agents ranges from about 1 µm to about 3,500 µm beyond the stratum corneum, but still within the viable skin above the subcutaneous tissue, including each integer within the specified range. In some aspects, the depth in the viable skin for delivering one or more agents ranges from about 1 µm to about 2,000 µm beyond the stratum corneum, but still within the viable skin above the subcutaneous tissue, including each integer within the specified range. In some aspects, the depth in the viable skin for delivering one or more agents ranges from about 1 µm to about 1,000 µm beyond the stratum corneum, but still within the viable skin above the subcutaneous tissue, including each integer within the specified range. In some aspects, the depth in the viable skin for delivering one or more agents ranges from about 1 µm to about 500 µm beyond the stratum corneum, but still within the viable skin above the subcutaneous tissue, including each integer within the specified range. In some aspects, the depth in the viable skin for delivering one or more agents ranges from about 1 µm to about 250 µm beyond the stratum corneum, but still within the viable skin above the subcutaneous tissue, including each integer within the specified range. In some aspects, the depth in the viable skin for delivering one or more agents ranges from about 1 µm to about 100 µm beyond the stratum corneum, but still within the viable skin above the subcutaneous tissue, including each integer within the specified range. In some aspects, the depth in the viable skin for delivering one or more agents ranges from about 1 µm to about 50 µm beyond the stratum corneum, but still within the viable skin above the subcutaneous tissue, including each integer within the specified range. In some aspects, the average depth in the viable skin for delivering one or more agents is about 1 µm, about 5 µm, about 10 µm, about 20 µm, about 30 µm, about 40 µm, about 50 µm, about 60 µm, about 70 µm, about 80 µm, about 90 µm, about 100 µm, about 150 µm, about 250 µm, about 350 µm, about 450 µm, about 550 µm, about 650 µm, about 750 µm, about 850 µm, about 950 µm, about 1,000 µm, about 1,100 µm, about 1,200 µm, about 1,300 µm, about 1,400 µm, about 1,500 µm, about 1,600 µm, about 1,700 µm, about 1,800 µm, about 1,900 µm, about 2,000 µm, about 2,250 µm, about 2,500 µm, about 2,750 µm, about 3,000 µm, about 3,250 µm, about 3,500 µm, about 3,750 µm, about 4,000 µm, about 4,500 µm, or about 5,000 µm beyond the stratum corneum, but still within the viable skin above the subcutaneous tissue.

Non-limiting tests for assessing initial delivery depth in the skin may be invasive (e.g., a biopsy) or non-invasive (e.g., imaging). Conventional non-invasive optical methodologies may be used to assess delivery depth of an agent into the skin including remittance spectroscopy, fluorescence spectroscopy, photothermal spectroscopy, or optical coherence tomography (OCT). Imaging using methods may be conducted in real-time to assess the initial delivery depths. Alternatively, invasive skin biopsies may be taken immediately after administration of an agent, followed by standard histological and staining methodologies to determine delivery depth of an agent. For examples of optical imaging methods useful for determining skin penetration depth of administered agents see Sennhen, et al., *Skin Pharmacol.*, 6(2), 152-160 (1993), Gotter, et al., *Skin Pharmacol. Physiol.*, 21, 156-165 (2008), and Mogensen, et al., *Semin. Cutan. Med. Surg.*, 28, 196-202 (2009), each of which are incorporated by reference herein for their teachings thereof.

In some embodiments described herein are methods for the extended delivery (or administration) of one or more agents described herein. In some aspects, the one or more agents is delivered over a period of time from about 0.5 hours to about 72 hours, including each integer of time within the specified range. In some aspects, the one or more agents is delivered over a period of time from about 0.5 hours to about 48 hours, including each integer of time within the specified range. In some aspects, the one or more agents is delivered over a period time from about 0.5 hours to about 24 hours, including each integer of time within the specified range. In some aspects, the one or more agents is delivered over a period of time from about 0.5 hours to about 12 hours, including each integer of time within the specified range. In some aspects, the one or more agents is delivered over a period of time from about 0.5 hours to about 6 hours, including each integer of time within the specified range. In some aspects, the one or more agents is delivered over a period of time of about 0.5 hours, about 1 hours, about 1.5 hours, about 2 hours, about 2.5 hours, about 3 hours, about 3.5 hours, about 4 hours, about 4.5 hours, about 5 hours, about 6 hours, about 7 hours, about 8 hours, about 9 hours, about 10 hours, about 11 hours, about 12 hours, about 16 hours, about 20 hours, about 24 hours, about 28 hours, about 32 hours, about 36 hours, about 40 hours, about 44 hours, about 48 hours, about 52 hours, about 56 hours, about 60 hours, about 64 hours, about 68 hours, or about 72 hours.

In some embodiments described herein, one or more agents in a liquid carrier solution are administered to an initial approximate space in the skin. The one or more agents in a liquid carrier solution initially delivered to the skin (e.g., prior to any subsequent movement or diffusion) may be distributed within, or encompassed by an approximate three dimensional volume of the skin. Thus, as further described herein, the one or more initially delivered agents exhibits a Gaussian distribution of delivery depths and will also have a Gaussian distribution within a three dimensional volume of the skin tissue. In some aspects, the one or more agents in a liquid carrier solution may be administered to the skin, wherein the tissue volume comprising the one or more agents in a liquid carrier solution is about 0.7 mm$^3$ to about 2,500 mm$^3$, including each integer within the specified range. In some aspects, the one or more agents in a liquid carrier solution may be administered to the skin, wherein the total three dimensional surface area of the administered liquid carrier solution comprising the one or more agents is about 18 mm$^2$ to about 20,000 mm$^2$, including each integer within the specified range. In some aspects, the one or more agents in a liquid carrier solution may be administered to the skin, wherein the three dimensional surface area to volume ratio of the administered liquid carrier solution comprising the one or more agents is about 35 mm$^{-1}$ to about 5 mm$^{-1}$, including each integer within the specified range. The exemplified volume, surface area, and surface area to volume ratios may vary depending on the local physiological administration site, size of the delivery device, delivery depth, and disease to be treated.

The tissue volume, surface area, and surface area to volume ratio of a delivered agent may be determined by using standard geometric calculations following measuring the overall dimensions (width and length) of the delivery device in contact with the skin of a subject and the deepest delivery depth of an initially administered agent using the standard methods and techniques of measuring delivery depth as described herein.

In some embodiments described herein, multiple dosages of one or more agents in a liquid carrier solution as described herein is simultaneously administered to the skin for targeted delivery to one or more susceptible tumors. In some aspects, one or more agents in a liquid carrier solution are simultaneously administered in between 2 and 50,000 sub doses, including each integer within the specified range. In some aspects, one or more agents in a liquid carrier solution are simultaneously administered in between 2 and 25,000 sub doses. In some aspects, one or more agents in a liquid carrier solution are simultaneously administered in between 2 and 15,000 sub doses, including each integer within the specified range. In some aspects, one or more agents in a liquid carrier solution are simultaneously administered in between 2 and 10,000 sub doses, including each integer within the specified range. In some aspects, one or more agents in a liquid carrier solution are simultaneously administered in between 2 and 5,000 sub doses, including each integer within the specified range. In some aspects, one or more agents in a liquid carrier solution are simultaneously administered in between 2 and 1,000 sub doses, including each integer within the specified range. In some aspects, one or more agents in a 10 liquid carrier solution are simultaneously administered in between 2 and 500 sub doses, including each integer within the specified range. In some aspects, one or more agents in a liquid carrier solution are simultaneously administered in between 2 and 250 sub doses, including each integer within the specified range. In some aspects, one or more agents in a liquid carrier solution are simultaneously administered in between 2 and 150 sub doses, including each integer within the specified range. In some aspects, one or more agents in a liquid carrier solution are simultaneously administered in between 2 and 100 sub doses. In some aspects, one or more agents in a liquid carrier solution are simultaneously administered in between 2 and 50 sub doses, including each integer within the specified range. In some aspects, one or more agents in a liquid carrier solution are simultaneously administered in between 2 and 25 sub doses, including each integer within the specified range. In some aspects, one or more agents in a liquid carrier solution are simultaneously administered in between 2 and 15 sub doses, including each integer within the specified range. In some aspects, one or more agents in a liquid carrier solution are simultaneously administered in between 2 and 10 sub doses. In some aspects, one or more agents in a liquid carrier solution is simultaneously administered in about 2 sub doses, about 5 sub doses, about 10 sub doses, about 15 sub doses, about 20 sub doses, about 25 sub doses, about 30 sub doses, about 35 sub doses, about 40 sub doses, about 45 sub doses, about 50 sub doses, about 75 sub doses, about 80 sub doses, about 85 sub doses, about 90 sub doses, about 95 sub doses, about 100 sub doses, about 150 sub doses, about 200 sub doses, about 250 sub doses, about 300 sub doses, about 350 sub doses, about 400 sub doses, about 450 sub doses, about 500 sub doses, about 600 sub doses, about 700 sub doses, about 800 sub doses, about 900 sub doses, about 1,000 sub doses, about 2,000 sub doses, about 3,000 sub doses, about 4,000 sub doses, about 5,000 sub doses, about 6,000 sub doses, about 7,000 sub doses, about 8,000 sub doses, about 9,000 sub doses, about 10,000 sub doses, about 15,000 sub doses, about 20,000 sub doses, about 25,000 sub doses, about 30,000 sub doses, about 35,000 sub doses, about 40,000 sub doses, about 45,000 sub doses, or about 50,000 sub doses. In some aspects, the above described sub doses may be administered by a suitable delivery structure as further described herein.

In some embodiments described herein, the flow rate of one or more administered agents to the skin per single delivery structure as described herein may be about 0.01 µl per hour to about 500 µl per hour, including each integer within the specified range for the targeted delivery to one or more susceptible tumors. In some aspects, the controlled flow rate of one or more administered agents per single delivery structure as described herein may be about 0.01 µl per hour to about 250 µl per hour, including each integer within the specified range In some aspects, the controlled flow rate of one or more administered agents per single delivery structure as described herein may be about 0.01 µl per hour to about 150 µl per hour, including each integer within the specified range. In some aspects, the controlled flow rate of one or more administered agents per single delivery structure as described herein may be about 0.01 µl per hour to about 100 µl per hour, including each integer with in the specified range. In some aspects, the controlled flow rate of one or more administered agents per single delivery structure as described herein may be about 0.01 µl per hour to about 50 µl per hour, including each integer within the specified range. In some aspects, the controlled flow rate of one or more administered agents per single delivery structure as described herein may be about 0.01 µl per hour to about 25 µl per hour, including each integer within the specified range. In some aspects, the controlled flow rate of one or more administered agents per single delivery structure as described herein may be about 0.01 µl per hour, about 0.5 µl per hour, about 1 µl per hour, about 1.5 µl per hour, about 2 µl per hour, about 2.5 µl per hour, about 3 µl per hour, about 3.5 µl per hour, about 4 µl per hour, about 4.5 µl per hour, about 5 µl per hour, about 10 µl per hour, about 15 µl per hour, about 20 µl per hour, about 25 µl per hour, about 30 µl per hour, about 35 µl per hour, about 40 µl per hour, about 45 µl per hour, about 50 µl per hour, about 60 µl per hour, about 70 µl per hour, about 80 µl per hour, about 90 µl per hour, about 100 µl per hour, about 125 µl per hour, about 150 µl per hour, about 175 µl per hour, about 200 µl per hour, about 225 µl per hour, about 250 µl per hour, about 300 µl per hour, about 350 µl per hour, about 400 µl per hour, about 450 µl per hour, about 500 µl per hour.

In some embodiments described herein, the overall controlled flow rate of one or more administered agents to a subject as described herein may be from about 0.02 µl per hour to about 50,000 µl per hour, including each integer within the specified range, which results in uptake of the one or more agents by one or more susceptible tumors. In some aspects, the overall controlled flow rate of one or more administered agents described herein may be from about 0.02 µl per hour to about 25,000 µl per hour, including each integer with in the specified range. In some aspects, the overall controlled flow rate of one or more administered agents described herein may be from about 0.02 µl per hour to about 15,000 µl per hour, including each integer within the specified range. In some aspects, the overall controlled flow rate of one or more administered agents described herein may be from about 0.02 µl per hour to about 10,000 µl per hour, including each integer within the specified range. In some aspects, the overall controlled flow rate of one or more administered agents described herein may be from about 0.02 µl per hour to about 5,000 µl per hour, including each integer within the specified range. In some aspects, the overall controlled flow rate of one or more administered agents described herein may be from about 0.02 µl per hour to about 2,500 µl per hour, including each integer within the specified range. In some aspects, the overall controlled flow rate of one or more administered agents described herein may be from about 0.02 µl per hour to about 1,250 µl per hour, including each integer within the specified range. In some aspects, the overall controlled flow rate of one or more administered agents described herein may be from about 0.02 µl per hour to about 500 µl per hour, including each integer within the specified range. In some aspects, the overall controlled flow rate of one or more administered agents described herein may be from about 0.02 µl per hour to about 250 µl per hour, including each integer within the specified range. In some aspects, the overall controlled flow rate of one or more administered agents described herein may be from about 0.02 µl per hour to about 125 µl per hour, including each integer within the specified range. In some aspects, the overall controlled flow rate of one or more administered agents described herein may be from about 0.02 µl per hour to about 50 µl per hour, including each integer within the specified range. In some aspects, the overall controlled flow rate of one or more administered agents described herein may be from about 0.02 µl per hour to about 25 µl per hour, including each integer within the specified range. In some aspects, the overall controlled flow rate of one or more administered agents described herein may be from about 0.02 µl per hour to about 10 µl per hour, including each integer within the specified range. In some aspects, he overall controlled flow rate of one or more agents described herein may be about 0.02 µl per hour, about 0.5 µl per hour, about 1 µl per hour, about 1.5 µl per hour, about 2 µl per hour, about 2.5 µl per hour, about 3 µl per hour, about 3.5 µl per hour, about 4 µl per hour, about 4.5 µl per hour, about 5 µl per hour, about 10 µl per hour, about 15 µl per hour, about 20 µl per hour, about 25 µl per hour, about 30 µl per hour, about 35 µl per hour, about 40 µl per hour, about 45 µl per hour, about 50 µl per hour, about 60 µl per hour, about 70 µl per hour, about 80 µl per hour, about 90 µl per hour, about 100 µl per hour, about 125 µl per hour, about 150 µl per hour, about 175 µl per hour, about 200 µl per hour, about 225 µl per hour, about 250 µl per hour, about 300 µl per hour, about 350 µl per hour, about 400 µl per hour, about 450 µl per hour, about 500 µl per hour, about 550 µl per hour, about 600 µl per hour, about 650 µl per hour, about 700 µl per hour, about 750 µl per hour, about 800 µl per hour, about 850 µl per hour, about 900 µl per hour, about 950 µl per hour, about 1,000 µl per hour, about 1,250 µl per hour, about 1,500 µl per hour, about 1,750 µl per hour, about 2,000 µl per hour, about 2,250 µl per hour, about 2,500 µl per hour, about 2,750 µl per hour, about 3,000 µl per hour, about 3,250 µl per hour, about 3,500 µl per hour, about 3,750 µl per hour, about 4,000 µl per hour, about 4,250 µl per hour, about 4,500 µl per hour, about 4,750 µl per hour, about 5,000 µl per hour, about 5,500 µl per hour, about 6,000 µl per hour, about 6,500 µl per hour, about 7,000 µl per hour, about 7,500 µl per hour, about 8,000 µl per hour, about 8,500 µl per hour, about 9,000 µl per hour, about 9,500 µl per hour, about 10,000 µl per hour, about 10,000 µl per hour, about 20,000 µl per hour, about 30,000 µl per hour, about 40,000 µl per hour, or about 50,000 µl per hour.

In some embodiments described herein, the combined overall controlled flow rate of one or more agents administered to the skin of a subject as described herein may range from about 0.02 µl/hr/cm$^2$ to about 50,000 µl/hr/cm$^2$, including each integer within the specified range based on the total surface area of a delivery device that is in contact with the skin of the subject as further described herein. In the following aspects the rate of delivery based on the total surface areas described herein results in uptake of the one or more agents by one or more susceptible tumors. In one aspect, the total surface area of a delivery device refers to the two dimensional surface area of the delivery device backing substrate that is in contact with the skin of a subject. In another aspect, the total surface area of a delivery device refers to the combined total of the two dimensional cross sectional surface areas of each of the independent delivery structures that are in contact with the skin of a subject. In some aspects, the overall controlled flow rate of one or more administered agents described herein may range from about 0.02 µl/hr/cm$^2$ to about 50,000 µl/hr/cm$^2$, including each integer within the specified range. In some aspects, the overall controlled flow rate of one or more administered agents described herein may range from about 0.02 µl/hr/cm$^2$ to about 15,000 µl/hr/cm$^2$, including each integer within the specified range. In some aspects, the overall controlled flow rate of one or more administered agents described herein may range from about 0.02 µl/hr/cm$^2$ to about 10,000 µl/hr/cm$^2$, including each integer within the specified range. In some aspects, the overall controlled flow rate of one or more administered agents described herein may range from about 0.02 µl/hr/cm$^2$ to about 5,000 µl/hr/cm$^2$, including each integer within the specified range. In some aspects, the overall controlled flow rate of one or more administered agents described herein may range from about 0.02 µl/hr/cm$^2$ to about 2,500 µl/hr/cm$^2$, including each integer within the specified range. In some aspects, the overall controlled flow rate of one or more administered agents described herein may range from about 0.02 µl/hr/cm$^2$ to about 1,250 µl/hr/cm$^2$, including each integer within the specified range. In some aspects, the overall controlled flow rate of one or more administered agents described herein may range from about 0.02 µl/hr/cm$^2$ to about 500 µl/hr/cm$^2$, including each integer within the specified range. In some aspects, the overall controlled flow rate of one or more administered agents described herein may range from about 0.02 µl/hr/cm$^2$ to about 250 µl/hr/cm$^2$, including each integer within the specified range. In some aspects, the overall controlled flow rate of one or more administered agents described herein may range from about 0.02 µl/hr/cm$^2$ to about 125 µl/hr/cm$^2$, including each integer within the specified range. In some aspects, the overall controlled flow rate of one or more administered agents described herein may range from about 0.02 µl/hr/cm$^2$ to about 50 µl/hr/cm$^2$, including each integer within the specified range. In some aspects, the overall controlled flow rate of one or more administered agents described herein may range from about 0.02 µl/hr/cm$^2$ to about 25 µl/hr/cm$^2$, including each integer within the specified range. In some aspects, the overall controlled flow rate of one or more administered agents described herein may range from about 0.02 µl/hr/cm$^2$ to about 10 µl/hr/cm$^2$, including each integer within the specified range. In some aspects, the overall controlled flow rate of one or more administered agents described herein may range from about 0.02 µl/hr/cm² to about 5 µl/hr/cm², including each integer within the specified range. In some aspects, be overall controlled flow rate of one or more agents described herein may be about 0.02 µl/hr/cm², about 0.5 µl/hr/cm², about 1 µl/hr/cm², about 1.5 µl/hr/cm², about 2 µl/hr/cm², about 2.5 µl/hr/cm², about 3 µl/hr/cm², about 3.5 µl/hr/cm², about 4 µl/hr/cm², about 4.5 µl/hr/cm², about 5 µl/hr/cm², about 10 µl/hr/cm², about 15 µl/hr/cm², about 20 µl/hr/cm², about 25 µl/hr/cm², about 30 µl/hr/cm², about 35 µl/hr/cm², about 40 µl/hr/cm², about 45 µl/hr/cm², about 50 µl/hr/cm² about 60 µl/hr/cm², about 70 µl/hr/cm² about 80 µl/hr/cm², about 90 µl/hr/cm², about 100 µl/hr/cm², about 125 µl/hr/cm², about 150 µl/hr/cm², about 175 µl/hr/cm², about 200 µl/hr/cm², about 225 µl/hr/cm², about 250 µl/hr/cm², about 300 µl/hr/cm², about 350 µl/hr/cm², about 400 µl/hr/cm², about 450 µl/hr/cm², about 500 µl/hr/cm², about 550 µl/hr/cm², about 600 µl/hr/cm², about 650 µl/hr/cm², about 700 µl/hr/cm², about 750 µl/hr/cm², about 800 µl/hr/cm², about 850 µl/hr/cm², about 900 µl/hr/cm², about 950 µl/hr/cm², about 1,000 µl/hr/cm², about 1,250 µl/hr/cm², about 1,500 µl/hr/cm², about 1,750 µl/hr/cm², about 2,000 µl/hr/cm², about 2,250 µl/hr/cm², about 2,500 µl/hr/cm² about 2,750 µl/hr/cm², about 3,000 µl/hr/cm², about 3,250 µl/hr/cm², about 3,500 µl/hr/cm², about 3,750 µl/hr/cm², about 4,000 µl/hr/cm², about 4,250 µl/hr/cm², about 4,500 µl/hr/cm², about 4,750 µl/hr/cm², about 5,000 µl/hr/cm², about 5,500 µl/hr/cm² about 6,000 µl/hr/cm² about 6,500 µl/hr/cm², about 7,000 µl/hr/cm², about 7,500 µl/hr/cm², about 8,000 µl/hr/cm², about 8,500 µl/hr/cm², about 9,000 µl/hr/cm², about 9,500 µl/hr/cm², about 10,000 µl/hr/cm², about 20,000 µl/hr/cm², about 30,000 µl/hr/cm², about 40,000 µl/hr/cm², or about 50,000 µl/hr/cm².

In some embodiments described herein, the flow rate of one or more administered agents to the skin per single delivery structure as described herein may be about 0.01 µl per hour to about 500 µl per hour for the targeted delivery to one or more susceptible tumors.

In some embodiments described herein, the overall controlled flow rate of one or more administered agents to a subject as described herein may be from about 0.2 µl per hour to about 50,000 µl per hour, which results in uptake of the one or more agents by one or more susceptible tumors.

In some embodiments described herein, the combined overall controlled flow rate of one or more agents administered to the skin of a subject as described herein may range from about 0.02 µl/hr/cm² to about 50,000 µl/hr/cm² based on the total surface area of a delivery device that is in contact with the skin of the subject as further described herein. In one aspect, the total surface area of a delivery device refers to the two dimensional surface area of the delivery device backing substrate that is in contact with the skin of a subject. In another aspect, the total surface area of a delivery device refers to the combined total of the two dimensional cross sectional surface areas of each of the independent delivery structures that are in contact with the skin of a subject In some embodiments, the methods described herein provide for increased delivery of one or more agents to one or more lymphatic tissues for the targeted delivery to one or more susceptible tumors. In some aspects, the one or more agents travel through the lymphatic vasculature to one or more lymph nodes or one or more sites of a tumor. Without being bound by any theory, it is thought that the uptake of one or more agents by the lymphatic vasculature allows for delivery of the one or more agents to a location surrounding the susceptible tumor. Furthermore, tumors elicit lymphangiogenic responses, which may further increase the local lymphatic vasculature peripheral to a susceptible tumor allowing for drug delivery. Also, without being limited theory, it is further thought that increasing delivery of one or more bioactive agents (e.g., an anti-cancer agent) through the lymphatic vasculature may limit the metastatic dissemination of the tumor through the peripheral lymphatics by exerting a localized cytotoxic or therapeutic effect against potential metastatic cancer cells.

As further described herein, the physiology and hydrostatics of the lymphatic vasculature plays an important role in mammalian physiology and a yet untapped resource for the delivery of agents to tumors. The lymphatic vasculature comprises all of the lymphatic endothelial cells making up the lymphatic capillaries, larger lymphatic vessels, and collecting ducts. The fluid within the lymphatic vasculature and all bio-materials in this fluid eventually drain into one or more lymph nodes and ultimately into the blood stream to enter the systemic circulation. For a complete review of the lymphatic physiology, see, William N. Charman and Valentino J. Stella, Lymphatic Transport of Drugs (1992), which is incorporated by reference herein in its entirety.

The lymphatic system is a part of the immune system, protecting the body against infection and invasion by foreign organisms. Lymphocytes and macrophages patrol most of the body's tissues for invading viruses, bacteria, tumor cells, foreign proteins, toxins, damaged and dying cells, and foreign cells, including, foreign tissue grafts. Lymph vessels communicate with most tissues, transporting the lymph fluid that carries the immune cells to the lymph nodes and lymphatic organs, such as the spleen and thymus. The lymphatic vessels, also referred to as lymphatics or lymphatic vasculature, are a network of thin opaque tube-like structures that branch, like blood vessels, into tissues throughout the body. In mammals, including humans, most tissues and organs are drained by the lymphatic system.

Unlike the circulatory system, the lymphatic system is not closed and has no central pump. The lymphatic system forms a one-way flow system towards the heart. An elaborate network of lymph capillaries drains interstitial fluid from the tissues, after which, this fluid is referred to as lymph. The lymphatics enter all tissues except epithelia, brain, spinal cord, and bone marrow. A few connective tissues, such as cartilage and the cornea, have no blood vessels and also lack lymphatics. The lymph moves slowly and under low pressure from peristaltic contraction.

These lymphatic capillaries are ten to fifty micrometers in diameter. They start from a blind sac, or from anastomosing vessels. The endothelium is a single layer, with an incomplete basement membrane. They possess gap junctions that are highly permeable to plasma proteins and large particles, including, for example, carbon particles, pathogens, such as viruses, bacterial cells, and parasites, cells, including, for example, immune cells and tumor cells, and cellular debris. The lymphatic capillaries have one-way valves, which ensure flow is only in one direction. When the pressure of the interstitial fluid outside of the lymphatic capillary is greater than the pressure inside the capillary, the flaps open allowing for fluid to enter. Conversely, when the pressure is greater inside the capillary, the flap is forced shut, precluding any lymph from leaking out of the vessel. During inflammation, the capillaries develop further openings that allow for the uptake of even larger molecules and cellular debris.

Lymph flows from capillaries into collecting lymphatics where it encounters the first of many lymph nodes. These "afferent" lymphatic vessels bring lymph to a lymph node and the "efferent" lymphatic vessels take the lymph away from a lymph node. Lymph is a colorless, watery fluid originating from interstitial fluid. Lymph originates as blood plasma lost from the capillary beds of the circulatory system, which leaks out into the surrounding tissues. Although the capillaries of the circulatory system lose only about 1% of the volume of the fluid that passes through them to the interstitial tissue; however, so much blood circulates that the cumulative fluid loss in the average human body is about three liters per day. The lymphatic system recaptures this fluid by diffusion into lymph capillaries, and filters it through the various lymph nodes and returns it to the circulatory system by way of the thoracic duct. Once within the lymphatic system the fluid is called lymph, and has almost the same composition as the original interstitial fluid.

Lymphatic capillaries are ubiquitous found throughout the body. Non-limiting examples of such locations include the viable skin (dermis), tendons, striated muscle, muscle sheaths, the periosteum of bone, joint capsules, under the mesothelium lining of pleural, peritoneal, and pericardial cavities, the alimentary canal, salivary glands, liver, spleen, nasal cavity, trachea, bronchi, thyroid gland, thymus, adrenal gland, kidney, bladder, urethra, prostate, testis, uterus, ovary, and heart.

The lymph nodes filter lymph, with an internal honeycomb of connective tissue filled with lymphocytes that collect and destroy bacteria and viruses. Lymph nodes also produce lymphocytes and antibodies. When the body is fighting an infection, these lymphocytes multiply rapidly and produce a characteristic swelling of the lymph nodes. Lymph is transported to progressively larger lymphatic vessels culminating in the right lymphatic duct (for lymph from the right upper body) and the thoracic duct (for the rest of the body). These ducts drain into the circulatory system at the right and left subclavian veins, near the shoulders. Along the network of lymphatic vessels are a series of various lymphatic tissues and organs, including lymphatic nodules, Peyer's patches, tonsils, lymph nodes, the thymus, and the spleen.

Lymphatic nodules are transient clusters of lymphocytes that form at sites of infection and then disappear. No capsule or external covering separates nodules from the surrounding cells and fluids, which percolates directly into the nodules. The lymph nodes encapsulate many lymphatic nodules within a tough capsule and are supplied with blood vessels and lymphatics. Lymph nodes filter the lymph delivered to them by lymphatic vessels. Thus, lymph nodes filter the lymph draining from the lymphatic capillary bed in which the lymph node is situated. Peyer's patches are larger nodular clusters of lymphocytes located in the walls of the intestines and the tonsils are pockets of nodular tissue enfolded into the mucosa of the pharynx. Peyer's patches and the tonsils are situated to intercept antigens from the digestive and respiratory tracts, respectively.

The spleen, lymph nodes, and accessory lymphoid tissue (including the tonsils and appendix) are the secondary lymphoid organs. These organs are made up of a scaffolding of connective tissue that supports circulating B- and T-lymphocytes and other immune cells, including, for example, macrophages, dendritic cells, and eosinophils. When microorganisms invade the body or the body encounters other antigens, the antigens are typically transported from the tissue to the lymph. The lymph is carried in the lymph vessels to regional lymph nodes.

In the lymph nodes, the macrophages and dendritic cells phagocytose antigens, process antigens, and present antigens to lymphocytes, which can then start producing antibodies or serve as memory cells to recognize the antigens again in the future. Lymph and lymphoid tissue thus contain antibodies and immune cells.

There is a broad range of lymphatic absorption rates of fluid from the interstitial tissues. For example, it has been estimated that the percentage of water being evacuated from intestinal location via the lymphatics ranges anywhere from 1% to nearly 85% with other estimates indicating that the lymphatic system is responsible for absorbing between 15 and 20% of interstitial fluids. This discrepancy is likely due to the immediate physiological state of the lymphatic tissue measured.

Lymphatic capillaries are distributed widely throughout the skin in mammals. Particularly, certain areas such as the fingers and palms and plantar surfaces of the feet and toes and the scrotum have been found to have the highest distribution of lymphatics. The skin lymphatics consist principally of superficial lymphatic plexus in the dermis extending upwards to the outer two thirds portions of the dermal structure into the papillary dermis. Deeper plexus lie within the dermis near the subcutaneous tissue boundary in areas of the reticular dermis. In general, very little or no lymphatic tissue is found within the epidermis or subcutaneous tissue layers. The lymphatics are typically more uniform in areas of the skin that have thicker dermal layers (e.g., the palmar surface of the hands and plantar surface of the feet). Similar to the intestinal tissues, absorption of interstitial fluid and proteins in the skin is highly variable, for example, in animal models the lymph flow in skin areas is approximately 1 ml/hr/100 g of tissue, which may increase by over 10 fold depending on the local physiology surrounding the lymphatic vasculature. Various factors have been found to affect lymphatic absorption including venous pressure, contraction of surrounding tissues and blood vessels, and respiration rates. For example, Starling's equation describes the generation of interstitial fluid by the competition of hydrostatic and oncotic forces across semipermeable capillary walls. Thus, increased hydrostatic pressure or reduced oncotic pressure within a blood vessel, or increased capillary permeability, will tend to promote interstitial fluid volume and subsequent fluid absorption by the lymphatic capillaries or result in oedema.

The absorption of proteins and lipids is likewise highly varied and depends largely on fluid absorption rates, location within the skin, and molecular size. In general, the size and lipo or hydrophilicity of a molecule plays a large role in its relative absorption. For example, and without being limited by any theory, it is thought that molecules smaller than 10 kDa are absorbed by the blood capillaries and lymphatic capillaries at approximately the same rate, whereas molecules larger than 20 kDa may more likely enter into the lymphatics, depending on the physiological status of a given local lymphatic capillary as described above.

Thus, it has been widely appreciated that delivery to the lymphatic system would be highly desirable due to the ubiquitous nature of the lymphatic capillaries and the capability to absorb a plethora of differently sized agents. The above mentioned involvement of the lymphatic system in inflammation and the occurrence and dissemination of various cancers lend an important alternative route for both the local and systemic treatment of cancer and cancer tumors.

In some embodiments described herein, one or more agents are directly delivered to a position within the epidermis. In some aspects, the one or more agents diffuse, move, flow, or migrate to a position in proximity to the lymphatic vasculature. As described herein, this placement within the epidermis following the methods described herein results in the diffusion or movement of an agent through the epidermis and the viable epidermis and into the top layers of the dermis. This type of movement provided by the delivery methods described herein allows for direct contact of an agent to the most superficially present lymphatic capillary bed(s) or otherwise known as a lymphatic drainage bed or lymphatic capillary plexus, which physiologically functions to drain interstitial fluid for a given location to the rest of the lymphatic system. The localized delivery of one or more agents to a lymphatic capillary bed may result in the delivery of the agent to the first lymph nodes draining the lymphatic capillary bed, also referred to as "primary" lymph nodes. In some aspects, the localized delivery of one or more agents may also result in the delivery of the agent to additional lymph nodes downstream of the primary lymph nodes, also referred to as "secondary" lymph nodes. In some aspects, the agent may eventually enter the blood stream and be delivered systemically to one or more tumors. In some aspects, the agent may be delivered through the lymphatic vasculature inside of or in close proximity of a solid tumor or delivered to a tumor present within one or more lymph nodes.

Therefore, some embodiments described herein include methods for the localized delivery of one or more agents to a lymphatic tissue comprising one or more lymphatic capillaries, lymphatic nodules, lymph nodes, Peyer's patches, and/or the tonsils. In some aspects, the methods described herein are suitable for delivery to one or more lymph nodes in any tissue or region of the body. Suitable non-limiting examples comprise lymph nodes found in the hands, the feet, thighs (femoral lymph nodes), arms, legs, underarm (the axillary lymph nodes), the groin (the inguinal lymph nodes), the neck (the cervical lymph nodes), the chest (pectoral lymph nodes), the abdomen (the iliac lymph nodes), the popliteal lymph nodes, parasternal lymph nodes, lateral aortic lymph nodes, paraaortic lymph nodes, submental lymph nodes, parotid lymph nodes, submandibular lymph nodes, supraclavicular lymph nodes, intercostal lymph nodes, diaphragmatic lymph nodes, pancreatic lymph nodes, cisterna chyli, lumbar lymph nodes, sacral lymph nodes, obturator lymph nodes, mesenteric lymph nodes, mesocolic lymph nodes, mediastinal lymph nodes, gastric lymph nodes, hepatic lymph nodes, and splenic lymph nodes.

In some embodiments described herein are methods for delivering one or more agents to a susceptible lymphatic capillary plexus of a mammal for the targeted delivery of one or more agents to one or more susceptible tumors. In some aspects, the one or more agents are delivered to a tissue area having a susceptible lymphatic capillary plexus. In some aspects, the one or more agents are delivered to a viable area of the skin having a susceptible lymphatic capillary plexus. In some aspects, the susceptible lymphatic capillary plexus is located within a region of the viable dermis as described herein. In some aspects, the susceptible lymphatic capillary plexus readily absorbs one or more agents from the local surrounding interstitial tissue. In some aspects, the susceptible lymphatic capillary plexus is susceptible to absorbing one or more agents from the local surrounding interstitial tissue due to the local physiological environment. In some aspects, the local physiological environment is susceptible to absorbing one or more agents due to the presence of inflammation, higher interstitial fluid pressure compared to intralymphatic pressure, higher blood capillary fluid exchange rates, tissue contraction, respiration or a combination of factors thereof. In one aspect, the susceptible lymphatic capillary plexus has a lower pressure inside the lymphatic capillary compared to the surrounding interstitial fluid, wherein the one or more agents is located, thereby increasing the local absorption rate of the one or more agents by the lymphatic capillary plexus. In another aspect, the susceptible lymphatic capillary plexus and the one or more agents are located within an area of inflammation (e.g., stemming from an incidence of cancer), wherein local inflammation promotes the porosity of the lymphatic capillary plexus, thereby increasing the local absorption rate of one or more agents delivered thereto.

In some embodiments described herein are methods for delivering one or more agents to an area within the viable skin (e.g., the viable dermis) having one or more susceptible lymphatic capillary plexus. In some aspects, the delivery method comprises administering one or more agents in a suitable vehicle to the skin at a controlled rate, wherein the one or more agents surrounds one or more susceptible lymphatic capillary plexus. In some aspects, the one or more agents are delivered as a suspension or solution in a liquid carrier. Without being bound any theory, it is thought that administering one or more agents in a liquid carrier solution at a controlled rate, wherein the one or more lymphatic capillary plexus are surrounded by the solution containing the one or more agents may enhance its absorption by the lymphatic capillary plexus. Again, without being bound by any theory, it is thought that the absorption of solution containing the one or more agents may be due to increases in the local dermal interstitial fluid pressure around the lymphatic capillary plexus.

In some embodiments described herein, are methods for matching the physiological absorption rate of one or more susceptible lymphatic capillary plexus with a liquid carrier solution having one or more agents. In some aspects described herein, the methods for matching the tissue absorption rate of a susceptible lymphatic capillary plexus comprises increasing the local tissue fluid pressure or tissue hydrostatic pressure surrounding one or more lymphatic capillary plexus. The absorption rate of a lymphatic capillary plexus will depend upon numerous factors as further described herein (e.g., vascular capillary flow rates and filtration rates, tissue oncotic pressure and hydrostatic pressure, and tissue compliance, etc.). Without being bound by any theory, generally a relatively small increase in local interstitial tissue hydrostatic pressure increases the rate of lymphatic absorption. At lower tissue interstitial tissue absorption rates, the lymphatics are the primary route of fluid removal. Various proteins and other bioparticles are carried with the interstitial fluid as it drains from the interstitial tissues fluids into the lymphatic capillaries. The resulting increases in tissue hydrostatic pressure without a significant lowering of the tissue oncotic pressure preferentially forces fluid into the lymphatics and not the blood capillaries due to the general increased hydraulic conductance of the lymphatic vessels. In contrast, at relatively higher interstitial tissue absorption rates, the capillaries are generally the principal route of fluid removal. This is typically because as increased fluid is pushed into the interstitial tissues, the tissue oncotic pressure decreases forcing fluid into the blood capillaries due to the relatively high blood capillary oncotic pressure. Furthermore, the presence of intermediate to high levels of interstitial tissue fluid increases pressure on the extracellular matricis increasing tissue compliance (e.g., tissue expansion) and general lowering of hydrostatic pressure. This results in decreased lymphatic drainage. Thus, interstitial hydrostatic and oncotic pressure exert forces on capillary walls, whereas only tissue pressure has an impact on lymphatic draining.

In some embodiments described herein, the administration of a fluid containing one or more agents in a liquid carrier solution achieves an increase in the local dermal interstitial fluid pressure to promote lymphatic uptake of one or more agents. Without being limited by any theory, it is thought that interstitial fluid pressures greater than about 1 mmHg to about 3 mmHg results in interstitial fluid (e.g., dermal interstitial fluid) lymphatic draining. This amount of pressure results in the opening of the pressure responsive lymphatic valves as described herein allowing for interstitial fluid draining into the lymphatic capillaries. In some aspects, the area of the dermis, in which there is an increased dermal interstitial fluid pressure due to the administration of one or more agents described herein is below the administration site within the epidermis. In some aspects, the specific interstitial tissue pressure values maybe from about 1 mmHg to about 15 mmHg. In some aspects, the interstitial tissue pressure values maybe increased by the methods described herein to be from about 1 mmHg to about 10 mmHg. In some aspects, the specific interstitial tissue pressure values maybe increased by the methods described herein to be from about 1 mmHg to about 5 mmHg. In some aspects, the specific interstitial tissue pressure values maybe increased by the methods described herein to be greater than about 1 mmHg, greater than about 2 mmHg, greater than about 3 mmHg, greater than about 4 mmHg, greater than about 5 mmHg, greater than about 6 mmHg, greater than about 7 mmHg, greater than about 8 mmHg, greater than about 9 mmHg, greater than about 10 mmHg, greater than about 11 mmHg, greater than about 12 mmHg, greater than about 13 mmHg, greater than about 14 mmHg, greater than about 15 mmHg, greater than about 16 mmHg, greater than about 17 mmHg, greater than about 18 mmHg, greater than about 19 mmHg, or greater than about 20 mm Hg.

Any method for assessing interstitial fluid pressure known in the art may be used. For example, the micropipette, the wick-in-needle, or wick catheter techniques have shown high levels of intra assay precision and may be used to assess hydrostatic pressure surrounding a section of a probe inserted in to the interstitial space of a subject (e.g., the dermal interstitial space) while administering an agent or following the administration of an agent using the methods described herein. See, for example, Wiig and Swartz., Phsiol. Rev., 1005-1060, (2012), which is incorporated by reference herein for its teachings thereof.

In some embodiments described herein, the methods for controlled delivery described herein result in one or more active drug substances being deposited in one or more lymph nodes or lymphatic tissues. In some aspects, the concentration of the one or more active drug substances is about 0.5% to about 75% of the initial dosage per gram of lymph node tissue, including each integer within the specified range. In some aspects, the concentration of the one or more active drug substances is about 0.5% to about 50% of the initial dosage per gram of lymph node tissue, including each integer within the specified range. In some aspects, the concentration of the one or more active drug substances is about 0.5% to about 25% of the initial dosage per gram of lymph node tissue, including each integer within the specified range. In some aspects, the concentration of the one or more active drug substances is about 0.5% to about 15% of the initial dosage per gram of lymph node tissue, including each integer within the specified range. In some aspects, the concentration of the one or more active drug substances is about 0.5% to about 10% of the initial dosage per gram of lymph node tissue, including each integer within the specified range. In some aspects, the concentration of the one or more active drug substances is about 0.5% to about 5% of the initial dosage per gram of lymph node tissue, including each integer within the specified range. In some aspects, the concentration of the one or more active drug substances is about 10% to about 60% of the initial dosage per gram of lymph node tissue, including each integer within the specified range. In some aspects, the concentration of the one or more active drug substances is about 30% to about 55% of the initial dosage per gram of lymph node tissue, including each integer within the specified range. In some aspects, the concentration of the one or more active drug substances is about 40% to about 50% of the initial dosage per gram of lymph node tissue, including each integer within the specified range. In some aspects, the concentration of the one or more active drug substances is about 0.5%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, or about 75% of the initial dosage per gram of lymph node tissue.

In some embodiments described herein, the methods for controlled delivery described herein result in one or more active drug substances being deposited in one or more lymph nodes, wherein the ratio of the initial dose of one or more agents localized per gram of lymph node tissue to whole blood tissue is from about 2:1 to about 50:1 after about 36 hours, including all ratios within the specified range. In some aspects, the ratio of the initial dose of one or more agents localized per gram of lymph node tissue to whole blood tissue is from about 2:1 to about 25:1 after about 36 hours, including all ratios within the specified range. In some aspects, the ratio of the initial dose of one or more agents localized per gram of lymph node tissue to whole blood tissue is from about 2:1 to about 15:1 after about 36 hours, including all ratios within the specified range. In some aspects, the ratio of the initial dose of one or more agents localized per gram of lymph node tissue to whole blood tissue is from about 2:1 to about 10:1 after about 36 hours, including all ratios within the specified range. In some aspects, the ratio of the initial dose of one or more agents localized per gram of lymph node tissue to whole blood tissue is from about 2:1 to about 5:1 after about 36 hours, including all ratios within the specified range. In some aspects, the ratio of the initial dose of one or more agents localized per gram of lymph node tissue to whole blood tissue is about 2:1, about 3:1, about 4:1, about 5:1, about 6:1, about 7:1, about 8:1, about 9:1, about 10:1, about 12:1, about 14:1, about 16:1, about 18:1, about 20:1, about 25:1, about 30:1, about 35:1, about 40:1, about 45:1, or about 50:1.

In some embodiments described herein, the methods for controlled delivery described herein result in one or more active drug substances being deposited in one or more lymph nodes, wherein the ratio of the initial dose of one or more agents localized per gram of lymph node tissue to the skin is from about 0.1:1 to about 3:1 after about 36 hours, including all ratios within the specified range. In some aspects, the ratio of the initial dose of one or more agents localized per gram of lymph node tissue to the skin is from about 0.25:1 to about 3:1 after about 36 hours, including all ratios within the specified range. In some aspects, the ratio of the initial dose of one or more agents localized per gram of lymph node tissue to the skin is from about 0.5:1 to about 3:1 after about 36 hours, including all ratios within the specified range. In some aspects, the ratio of the initial dose of one or more agents localized per gram of lymph node tissue to the skin is from about 1:1 to about 3:1 after about 36 hours, including all ratios within the specified range. In some aspects, the ratio of the initial dose of one or more agents localized per gram of lymph node tissue to the skin is about 0.1:1, about 0.2:1, about 0.4:1, about 0.6:1, about 0.8:1, or about 1:1, about 2:1, or about 3:1.

Non-invasive quantification methods for drug biodistribution and absorption pharmacokinetics by tissues are well known and are used for assessing the percentage of absorbed drug per initial dose per gram of tissue. The percent initial dosage of one or more agents delivered per gram of lymph node tissue as described herein may be quantified by directly labelling the one or more agents with a detectable radio label followed by administration of the agent using the methods described herein. The imaging and quantification of the radio labelled agent may be assessed using standard positron emission tomography (PET) or single-photon emission computed tomography (SPECT), or a combination of these techniques with X-Ray computed tomography (CT) or magnetic resonance imaging (MRI) see, for example, Ding and Wu., *Theranostics,* 2(11), 1040-1053 (2012), which is incorporated by reference herein for its teachings thereof. Useful radiolabels may comprise short or long lived isotopes, such as $^{11}$C, $^{15}$O, $^{18}$F, $^{68}$Ga, $^{64}$Cu, $^{76}$Br, $^{89}$Zr, $^{124}$I. The selected radiolabel will depend on the agent being tested and specific labelling protocols well known in the art. The percent absorbed initial dose/gram of lymph node tissue measured initially using either PET or SPECT imaging may be calculated using standard radiopharmaceutical dosimetry and tissue density tables, see, Bolch, et al., *J. Nucl. Med.,* 50(3), 477 (2009), which is incorporated by reference herein for its teachings thereof.

Other comparative methodologies may be utilized to assess the amount of drug per gram of tissue delivered to a lymphatic tissue. Suitable comparative methodologies comprise radiolabelling one or more agents with any of the above described short or long lived isotopes above and administering the labelled one or more agents using the methods described herein to a suitable comparative test subject. The subject may comprise a laboratory animal such as a rat, guinea pig, mouse, or monkey. To determine the biodistribution and percent of an initial dose delivered per gram of lymphatic tissue, lymphatic tissue (e.g., one or more lymph nodes) amongst other relative organs may be harvested from the subject animal and the specific radioactivity counts within that tissue may be measured and quantified using standard well known techniques and compared to the radioactivity measurements of the initial dosage.

In some embodiments described herein, the methods for controlled delivery described herein result in more of the initial dosage of one or more agents being absorbed by one or more susceptible lymphatic capillary plexus compared to other traditional delivery routes, such as intravenous (i.v.), subcutaneous (s.c.), intramuscular (i.m.), or intradermal (i.d.) injection routes or traditional transdermal patches. In some aspects, the controlled delivery methods described herein result in approximately a 1.25 fold to about 50 fold increases in the lymphatic delivery of one or more agents compared to i.v., s.c., i.m., or i.d. parenteral delivery routes, including each integer within the specified range. In some aspects, the controlled delivery methods described herein result in approximately a 1.25 fold to about 20 fold increase in the lymphatic delivery of one or more agents compared to i.v., s.c., i.m., or i.d. parenteral delivery routes, including each integer within the specified range. In some aspects, the controlled delivery methods described herein result in approximately a 1.25 fold to about 10 fold increase in the lymphatic delivery of one or more agents compared to i.v., s.c., i.m., or i.d. parenteral delivery routes, including each integer within the specified range. In some aspects, the controlled delivery methods described herein result in approximately a 1.25 fold to about 5 fold increase in the lymphatic delivery of one or more agents compared to i.v., s.c., i.m., or i.d. parenteral delivery routes, including each integer within the specified range.

Assessing the uptake and comparison of an agent delivered using the methods described herein by one or more lymphatic capillary plexus may be determined by using one or more imaging agents attached to an agent or bioactive agent being delivered using the methods described herein. These imaging agents can be used to image the lymphatic capillaries and tissues, for example, one or more lymphatic capillary plexus or lymph node tissues. Suitable imaging agents may be any agent that is bio-compatible and has no biological activity or side effects. Exemplary and non-limiting imaging agents may be one or more agents used for direct or indirect X-ray lymphangiography imaging, one or more contrast agents used for magnetic resonance imaging (MRI), one or more fluorescent imaging agents for fluorescence microlymphangiography (FML), or one or more fluorescent imaging agent excitable by tissue-penetrating near-infrared light (NIR) for use in CG lymphography. The techniques and agents used for lymphatic imaging are known in the art, see, for example, Sevick-Muraca, et al., *J. Clin Invest.,* 124(3), 905-914 (2014), which is incorporated by reference herein for its teachings thereof. Standard image analysis algorithms and software may be used to calculate fluorophore intensity of a delivered agent that is labelled or tagged with an imaging agent as described above and compared to traditional i.v., s.c., i.m., or i.d. parenteral delivery routes.

In some embodiments, the methods for controlled delivery described herein result in an equivalent blood serum absorption rate of one or more agents described herein compared to i.v., s.c., i.m., or i.d. parenteral delivery routes, while retaining relatively higher rates of lymphatic delivery as described herein. Without being bound by any theory, the rate of delivery may be due to the lymphatic circulation of one or more agents through the thoracic duct and into the blood circulation. Standard highly accurate and precise methodologies for measuring blood serum concentration and therapeutic monitoring at desired time points may be used that are well known in the art, such as, but not limited to, radioimmunoassays, high-performance liquid chromatography (HPLC), fluorescence polarization immunoassay (FPIA), enzyme immunoassay (EMIT) or enzyme-linked immunosorbent assays (ELISA). For calculating the absorption rate using the methods described above, the drug concentration at several time points should be measured starting immediately following administration and incrementally thereafter until a $C_{max}$ value can be established and the associated absorption rate calculated.

In some embodiments described herein are methods for the controlled delivery of one or more agents in a liquid carrier solution as described herein to the skin for the targeted delivery of one or more agents to one or more susceptible tumors. In some aspects, the methods comprise penetrating at least a most superficial layer of epidermis with a delivery structure described herein, contacting the epidermis with one or more permeability enhancers, and administering one or more agents in a liquid carrier solution in between about 2 and 50,000 sub doses, wherein the sub doses are administered to the skin (e.g., non-viable epidermis and/or viable epidermis and/or viable dermis) at a depth of about 10 µm to about 4,500 µm or about 1 µm to about 4,000 µm beyond a most superficial layer of the epidermis, but still within the viable skin above the subcutaneous tissue; and wherein the administration comprises one or more of (a) an administration flow rate that matches the tissue lymphatic drainage rate; (b) an overall administration flow rate of about 0.02 µl/hr/cm² to about 50,000 µl/hr/cm² based on the surface area of the delivery device or delivery structures; (c) an interstitial fluid pressure greater than about 2 mmHg in the local vicinity of one or more susceptible lymphatic capillary plexus; and (d) delivering the one or more agents within a liquid carrier to the skin, wherein the delivered fluid is in contact with or encompassed by a three dimensional tissue volume of about 0.7 mm³ to about 2,500 mm³.

In some embodiments described herein are methods for the controlled delivery of one or more active drug substances to the skin. In some aspects, an overall dose of one or more active drug substances in a liquid carrier is delivered to one or more susceptible tumors. In some aspects, an overall dose of one or more active drug substances in a liquid carrier is delivered first to one or more susceptible lymphatic capillary plexus followed by a targeted delivery to one or more susceptible tumors. This overall dose may comprise between 2 and 50,000 sub doses as described herein. In some aspects, the overall dose of one or more active drug substances may comprise about 0.0001 mg/kg of body weight to about 100 mg/kg body weight, including each integer within the specified range. In some aspects, the overall dose of one or more active drug substances may comprise about 0.001 mg/kg of body weight to about 100 mg/kg body weight, including each integer within the specified range. In some aspects, the overall dose of one or more active drug substances may comprise about 0.01 mg/kg of body weight to about 100 mg/kg body weight, including each integer within the specified range. In some aspects, the overall dose of one or more active drug substances may comprise about 0.1 mg/kg of body weight to about 100 mg/kg body weight, including each integer within the specified range. In some aspects, the overall dose of one or more active drug substances may comprise about 0.1 mg/kg of body weight to about 50 mg/kg body weight, including each integer within the specified range. In some aspects, the overall dose of one or more active drug substances may comprise about 0.1 mg/kg of body weight to about 25 mg/kg body weight, including each integer within the specified range. In some aspects, the overall dose of one or more active drug substances may comprise about 0.1 mg/kg of body weight to about 10 mg/kg body weight, including each integer within the specified range. In some aspects, the overall dose of one or more active drug substances may comprise about 0.1 mg/kg of body weight to about 5 mg/kg body weight, including each integer within the specified range. In some aspects, the overall dose of one or more active drug substances may comprise about 0.0001 mg/kg, about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, or about 100 mg/kg.

In some embodiments described herein are methods for the controlled delivery of one or more active drug substances to the skin. In some aspects, an overall dose of one or more active drug substances in a liquid carrier is delivered to one or more susceptible tumors. In some embodiments, the methods for controlled delivery described herein result in an equivalent blood serum absorption rate of one or more agents described herein compared to i.v., s.c., i.m., or i.d. parenteral delivery routes, while retaining relatively higher rates of lymphatic delivery as described herein. Without being bound by any theory, the rate of delivery may be due to the lymphatic circulation of one or more agents through the thoracic duct and into the blood circulation.

In some embodiments, the methods for controlled delivery described herein result in physiologically prolonged levels of a bioactive agent (e.g., an active drug substance) above a known efficacious therapeutic threshold. In some aspects, the methods of controlled delivery described herein reduce or prevent the bolus administration of one or more active drug substances described herein. In some aspects, this may result in an increased safety profile of one or more bioactive agents by limiting potentially dangerous spikes in the systemic plasma circulation of one or more bioactive agents. Furthermore, the controlled delivery methods described herein may further increase the therapeutic ratio of one or more administered active drug substances by lowering the dose needed for a therapeutic or beneficial effect.

In some embodiments, the controlled delivery methods described herein result in one or more agents being retained at the site of the disease (e.g., within one or more lymph nodes), and not spread systemically resulting in a reduced occurrence of known side effects of the active drug substance. For example, diseases involving inflammation (e.g., cancer, infection, arthritis), one or more agents may be absorbed by a susceptible lymphatic capillary plexus and distributed to the sites of inflammation and not further distribute into the systemic circulation. The one or more agents may be distributed systemically by circulating through the lymphatic vasculature and lymphatic tissues through the thoracic duct and into the systemic blood circulation. Alternatively, the one or more agents may be distributed systemically by being directly absorbed by one or more susceptible blood capillary plexus. In some aspects, the one or more agents may then be absorbed by one or more susceptible tumors in a subject by extravasating from the tumor blood vasculature and into the tumor stroma.

In some embodiments, the methods for controlled delivery described herein result in relatively short time to maximal therapeutic efficacy or $T_{max}$, while retaining physiologically prolonged levels of one or more active drug substances above the efficacious therapeutic threshold. The $T_{max}$ may be independent of the $C_{max}$ or total blood serum concentration of an active drug substance and can be assessed by the perception of amelioration of a disease or condition.

In some embodiments described herein, the one or more bioactive agents delivered to the skin and subsequently one or more susceptible tumors by the methods described herein may comprise an active drug substance. For example, the active drug substance may be a compound (e.g., a small molecule), that is capable of acting on a cellular receptor or surface protein and function as an agonist, antagonist, inverse agonist, etc., which results in the modification of a disease pathway and an often efficacious and beneficial outcome for a subject afflicted with a disease or disorder as described herein. The active drug substance may exhibit toxicity to cancer cells or have bactericidal or anti-viral activity. Suitable active drug substances will depend on the disease or disorder being treated and the tolerance of the subject for receiving a particular active drug substance. Suitable active drug substances described herein may be administered regardless of whether the active drug substance is hydrophilic, lipophilic, or amphipathic. Active drug substances may be poorly or highly soluble in an aqueous environment or demonstrate low or high systemic permeability (e.g., any BCS Class I, II, III, or IV drug). Furthermore active drug substances described herein may also comprise any protein drug, such as an antibody (e.g., a humanized antibody).

Exemplary active drug substances may comprises a small molecule. In some aspects, the small molecule may have a molecular weight of about 50 g/mol to about 1,000 g/mol (i.e., ≈50 Da –1,000 Da), including each integer within the specified range. In some aspects, the small molecule may have a molecular weight of about 50 g/mol, about 100 g/mol, about 150 g/mol, about 200 g/mol, about 250 g/mol, about 300 g/mol, about 350 g/mol, about 400 g/mol, about 450 g/mol, about 500 g/mol, about 550 g/mol, about 600 g/mol, about 650 g/mol, about 700 g/mol, about 750 g/mol, about 800 g/mol, about 850 g/mol, about 900 g/mol, about 950 g/mol, or about 1000 g/mol.

Other suitable active drug substances may comprise a larger compound or protein. In some aspects, the compound or protein may have an atomic mass of about 1 kDa to about 250 kDa, including each integer within the specified range. In some aspects, the compound or protein may have an atomic mass of about 1 kDa, about 5 kDa, about 10 kDa, about 15 kDa, about 20 kDa, about 25 kDa, about 50 kDa, about 75 kDa, about 100 kDa, about 125 kDa, about 150 kDa, about 175 kDa, about 200 kDa, about 225 kDa, or about 250 kDa.

In some embodiments described herein are methods for administering one or more bioactive agents to an animal, preferably a mammal, and most preferably a human, for preventing, treating, or ameliorating one or more symptoms associated with a disease, disorder, or infection, by delivering the one or more bioactive agents to the skin of subject's skin. The methods described herein are useful for the treatment or prevention of a disease or disorder of the lymphatic system, primary or metastatic neoplastic disease (i.e., cancer). The bioactive agent's may be provided in pharmaceutically acceptable compositions or formulations as known in the art or as described herein.

In some embodiments described herein, the one or more bioactive agents are present in a liquid carrier as a substantially dissolved solution, a suspension, or a colloidal suspension. Any suitable liquid carrier solution may be utilized that meets at least the United States Pharmacopeia (USP) specifications, and the tonicity of such solutions may be modified as is known, see, for example, Remington: The Science and Practice of Pharmacy (Lloyd V. Allen Jr. ed., $22^{nd}$ ed. 2012. Exemplary non-limiting liquid carrier solutions may be aqueous, semi-aqueous, or non-aqueous depending on the bioactive agent(s) being administered. For example, an aqueous liquid carrier may comprise water and any one of or a combination of a water-miscible vehicles ethyl alcohol, liquid (low molecular weight) polyethylene glycol, and the like. Non aqueous carriers may comprise a fixed oil, such as corn oil, cottonseed oil, peanut oil, or sesame oil, and the like. Suitable liquid carrier solutions may further comprise any one of a preservative, antioxidant, complexation enhancing agent, a buffering agent, an acidifying agent, saline, an electrolyte, a viscosity enhancing agent, a viscosity reducing agent, an alkalizing agent, an antimicrobial agent, an antifungal agent, a solubility enhancing agent or a combination thereof.

Some embodiments, described herein, include methods of treating, preventing, reducing the likelihood of, ameliorating, or managing a disease or disorder in a subject in need thereof, the method comprising administering to the subject a therapeutically effective dose or prophylactically effective dose of one or more bioactive agents (e.g., an active drug substance) to the skin of a subject in need thereof. In some aspects described herein are methods of treating, preventing, reducing the likelihood of, ameliorating, or managing cancer (e.g., treating one or more susceptible tumors or metastatic diseases thereof) in a subject, the method comprising administering to the subject a therapeutically effective dose or prophylactically effective dose of one or more bioactive agents (e.g., an active drug substance) to the skin of a subject in need thereof. In some aspects, the methods of treating or preventing a disease in a subject by delivering one or more bioactive agents to the skin of a subject is more effective than conventional delivery routes, e.g., i.v., s.c., i.m., or i.d. injections.

In some embodiments described herein, the methods for controlled delivery described herein result in one or more active drug substances being deposited in one or more susceptible tumors. In some aspects, the concentration of the one or more active drug substances delivered to one or more susceptible tumors is about 0.5% to about 75% of the initial dosage, including each integer within the specified range. Assessing the percent of a delivered agent to one or more tumors may be assessed by non-invasive techniques such as PET or SPECT or a combination of these techniques with XCT or MRJ as described herein. The percent initial dosage of the one or more agents delivered to one or more tumors herein may be quantified by directly labelling the one or more agents with a detectable radio label followed by administration of the agent using the methods described herein. The imaging and quantification of the radio labelled agent may be assessed using standard positron emission tomography (PET) or single-photon emission computed tomography (SPECT), or a combination of these techniques with X-Ray computed tomography (CT) or magnetic resonance imaging (MRI). See, for example, Ding and Wu., *Theranostics,* 2(11), 1040-20, 1053 (2012), which is incorporated by reference herein for its teachings thereof. Useful radiolabels may comprise short or long lived isotopes, such as, but not limited to, $^{11}C$, $^{15}O$, $^{18}F$, $^{68}Ga$, $^{64}Cu$, $^{76}Br$, $^{89}Zr$, and $^{124}I$. The selected radiolabel will depend on the agent being tested and specific labelling protocols that are well known in the art. The percent absorbed of the initial dose delivered to a tumor tissue measured initially using either PET or a combination of these techniques with X-Ray computed tomography (CT) or a combination of these techniques with X-Ray computed tomography (CT) or a combination of these techniques with X-Ray computed tomography (CT) or a combination of these techniques with X-Ray computed tomography (CT) or one combination of these techniques with X-Ray computed tomography (CT) or a combination of these techniques with X-Ray computed tomography (CT) or SPECT imaging may be calculated using standard radiopharmaceutical dosimetry and tissue density tables, see, Botch et al., *J. Nucl. Med.,* 50(3), 477 (2009), which is incorporated by reference herein for its teachings thereof.

In some aspects, the concentration of the one or more active drug substances delivered to one or more susceptible tumors is about 0.5% to about 50% of the initial dosage, including each integer within the specified range. In some aspects, the concentration of the one or more active drug substances delivered to one or more susceptible tumors is about 0.5% to about 25% of the initial dosage, including each integer within the specified range. In some aspects, the concentration of the one or more active drug substances delivered to one or more susceptible tumors is about 0.5% to about 15% of the initial dosage, including each integer within the specified range. In some aspects, the concentration of the one or more active drug substances delivered to one or more susceptible tumors is about 0.5% to about 10% of the initial dosage, including each integer within the specified range. In some aspects, the concentration of the one or more active drug substances delivered to one or more susceptible tumors is about 0.5% to about 5% of the initial dosage, including each integer within the specified range. In some aspects, the concentration of the one or more active drug substances delivered to one or more susceptible tumors is about 0.5%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, or about 75% of the initial dosage.

Assessing the percent of a delivered agent to one or more tumors may be assessed by non-invasive techniques such as PET or SPECT or a combination of these techniques with X-CT or MRI as described herein. The percent absorbed initial dose delivered to a tumor tissue measured initially using either PET or SPECT imaging may be calculated using standard radiopharmaceutical dosimetry and tissue density tables as described herein (e.g., as described for delivery to a lymphatic tissue).

Alternatively, to assess relative tumor drug concentration, one or more discovered tumors that have been treated or administered one or more labelled (e.g., radiolabelled) agents as described herein may be harvested from a subject. To determine the biodistribution and percent of an initial dose delivered per gram of tumor tissue, the specific radioactivity counts within that tissue may be measured and quantified using standard well known techniques and compared to the radioactivity measurements of the initial dosage.

In some embodiments described herein are methods for methods for increasing the amount of a bioactive agent delivered to one or more susceptible tumors. In some aspects, because more of the bioactive agent is targeted to the tumor, there is a smaller chance of incurring a deleterious side effect, while exhibiting increased therapeutic efficacy. In some aspects, the amount of bioactive agent required to treat one or more susceptible tumors is approximately 1% to about 75% of the dose of the identical bioactive agent required for treating one or susceptible tumors by conventional delivery routes; e.g., i.v., s.c., i.m., or i.d. injections, including each integer within the specified range. In some aspects, the amount of bioactive agent required to treat one or more susceptible tumors is approximately 1% to about 75% of the dose required for treating one or susceptible tumors by conventional delivery routes; e.g., i.v., s.c., i.m., or i.d. injections, including each integer within the specified range. In some aspects, the amount of bioactive agent required to treat one or more susceptible tumors is approximately 1% to about 50% of the dose required for treating one or susceptible tumors by conventional delivery routes; e.g., i.v., s.c., i.m., or i.d. injections, including each integer within the specified range. In some aspects, the amount of bioactive agent required to treat one or more susceptible tumors is approximately 1% to about 25% of the dose required for treating one or susceptible tumors by conventional delivery routes; e.g., i.v., s.c., i.m., or i.d. injections, including each integer within the specified range. In some aspects, the amount of bioactive agent required to treat one or more susceptible tumors is approximately 1% to about 10% of the dose required for treating one or susceptible tumors by conventional delivery routes; e.g., i.v., s.c., i.m., or i.d. injections, including each integer within the specified range. In some aspects, the amount of bioactive agent required to treat one or more susceptible tumors is approximately about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, or about 75% of the dose required for treating one or susceptible tumors by conventional delivery routes; e.g., i.v., s.c., i.m., or i.d. injections.

In some embodiments, the therapeutic efficacy of the one or more bioactive agents delivered to one or more susceptible tumors as described herein may be measured as a reduction in tumor size, decreased tumor metastasis, improvement in organ tissue function, reduction in associated side effects, reduced need for surgical intervention, improved quality of life, increased overall survival and increased refractory free survival or a mixture or combination thereof.

In some embodiments, the methods of targeted delivery of one or more bioactive agents to one or more susceptible tumors results in a greater decrease in size of one or more tumors or reduction in metastasis compared to conventional delivery routes; e.g., i.v., s.c., i.m., or i.d. injections. In some aspects, the size of the one or more tumors is reduced by about 5% to about 99% or more, including each integer within the specified range. In some aspects, the size of the one or more tumors is reduced by about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90% or about 95%, or about 99% or more.

Reductions in tumor size and reductions in metastasis (e.g., a solid tumor), and refractory free survival may be assessed and quantified by any common imaging method known in the art. For example magnetic resonance imaging (MRI) or magnetic resonance spectroscopy (MRS) may be used to non-invasively track and monitor tumor size or tumor metastasis or aggressiveness following administration of one or more bioactive agents. See, for example, Dynamic Contrast-Enhanced Magnetic Resonance Imaging in Oncology (Jackson et al. eds., 2013) and Gillies and Morse., *Annu. Rev. Biomed Eng.*, 7, 287-326 (2005), each of which is incorporated by reference herein for their respective teachings of MRI and MRS.

In some aspects described herein, the targeted delivery of one or more bioactive agents to one or more susceptible tumors results in decreased side effects. The reduction in side effects is due to the localization of one or more bioactive agents within a tumor or tumor metastasis. Furthermore, as described herein, a reduction in the amount of bioactive agent required to elicit the same therapeutic response (e.g., reduction in tumor size or reduction in metastatic potential) decreases the amount of potential side effects of any suitable delivered bioactive agent.

Therefore, the methods described herein provide for the targeted delivery of one or more bioactive agents to one or more susceptible tumors in a subject by the initial delivery to the skin with the methods described herein, results in previously unattained beneficial therapeutic outcomes, comprising dose sparing, increased drug efficacy, reduced side effects, reduced metastatic potential, reduced tumor associated inflammation, and prolonged survival of a subject. Accordingly, the methods described herein provide for increased deposition of therapeutic agents within one or more susceptible tumors when compared to i.v., s.c., i.m., or i.d. injection methods. Any suitable cancer, tumor or metastatic dissemination thereof may be treated by the methods described herein. Thus, the methods described herein provide for the treatment of a disease in a patient in need of treatment thereof; e.g., cancer, by improving the amount of the agent deposited within or in proximity of a tumor tissue.

In some embodiments the diffusion or movement of an administered agent through the epidermis may be increased by administering or contacting the epidermis of a subject with one or more permeability or penetration enhancers. In some aspects, the permeability or penetration enhancer may be chemical, physical, or electrical. The permeability enhancers function to increase the movement or diffusion of one or more agents through the stratum corneum of the epidermis and into to the viable epidermis. The permeability enhancers may further promote the movement or diffusion of one or more administered agents through the viable epidermis including the basement membrane of the viable epidermis and into the underlying viable dermis. See, for example, Prasunitz and Langer, *Nature Biotechnol*, 26(11), 1261-1268 (2008), which is incorporated by reference herein for its teachings of the use of epidermal permeability enhancers in transdermal drug delivery.

In some embodiments described herein, an effective amount of one or more chemical permeability enhancers may be delivered to the epidermis. Without being bound by any theory, it is thought that the chemical permeability enhancers described herein may promote the permeability of the stratum corneum to an administered agent by denaturing intracellular keratin, causing swelling due to hydration, affect desmosomes maintaining corneocyte adhesion, or modify barrier producing lipids within the lipid bilayer. Non-limiting examples of chemical permeability enhancers may include sulfoxides, such as dimethyl sulfoxide and dodecyl methyl sulfoxide; ureas; alcohols, such as ethanol, caprylic alcohol, and propylene glycol; pyrrolidones and derivatives, such as N-methyl-2-pyrrolidone and 2-pyrrolidone; azone and derivatives, such as 1-dodecylazacycloheptan-2-one; dioxolane derivatives; anionic, cationic, non-ionic, or zwitterionic surfactants, such as sodium lauryl sulfate, cetyltrimethyl ammonium bromide, sorbitan monolaurate, polysorbate 80, dodecyl dimethyl ammoniopropane sulfate; terpenes, such as menthol or limonene; fatty acids, such as oleic acid or undecanoic acid; or hydrative amounts of water.

In some embodiments described herein, a physical permeability enhancer may be used to increase the permeability of the epidermis to an administered agent. In some aspects, the physical permeability enhancer may rely on using sound, the application of electric fields, or specific structural interaction with the epidermis to increase the permeability of the epidermis. Non-limiting examples include sonophoresis (e.g., ultra sound), iontophoresis, electroporation, or nanostructured contact surfaces (e.g., nanotopograhy).

In some embodiments described herein, the methods for controlled delivery of one or more agents initially to skin for the targeted delivery to one or more tumors as described herein may comprise delivering one or more agents through a device comprising 2 or more delivery structures that are capable of penetrating the stratum corneum and obtaining a delivery depth and volume in the skin and controllably delivering one or more agents at the administration rates as described herein. The delivery structures may be attached to a backing substrate of the delivery device and arranged at one or a plurality of different angles for penetrating the stratum corneum and delivering the one or more agents. In some aspects, described herein the backing substrate comprising the delivery structures may be in contact with the skin of a subject and may have a cylindrical, rectangular, or geometrically irregular shape. The backing substrate further comprises a two dimensional surface area. In some aspects the two dimensional surface area may be from about 1 $mm^2$ to about 10,000 $mm^2$. In some aspects, the delivery structures may comprise any geometric shape (e.g., a cylindrical, rectangular or geometrically irregular shape). In addition, the delivery structures may comprise a length and cross sectional surface area. In some aspects, the delivery structures may have an overall length that is greater than a cross sectional diameter or width. In some other aspects, the delivery structures may have a cross sectional diameter or width greater than an overall length. In some aspects, the cross sectional width of each of the delivery structures may be from about 5 μm to about 140 μm and the cross sectional area may be from about 25 $μm^2$ to about 15,000 $μm^2$, including each integer within the specified range. In some aspects, the length of each of the delivery structures may be from about 10 μm to about 1,000 μm, including each integer within the specified range. The surface area and cross-sectional surface areas as described herein may be determined using standard geometric calculations known in the art.

The delivery structures described herein need not be identical to one another. A device having a plurality of delivery structures may each have various lengths, outer diameters, inner diameters, cross-sectional shapes, nanotopography surfaces, and/or spacing between each of the delivery structures. For example, the delivery structures may be spaced apart in a uniform manner, such as, for example, in a rectangular or square grid or in concentric circles. The spacing may depend on numerous factors, including height and width of the delivery structures, as well as the amount and type of an agent that is intended to be delivered through the delivery structures. In some aspects, the spacing between each delivery structure may be from about 1 μm to about 800 μm, including each integer within the specified range.

In some embodiments, the delivery structures may comprise an array of needles in fluid connection with a liquid carrier vehicle comprising one or more agents. In some aspects, the array of needles may comprise between 2 and 50,000 needles with structural means for controlling skin penetration and fluid delivery to the skin (e.g., penetrating and delivering to the skin), see, for example, US 20150367117, which is incorporated by reference herein in its entirety. In some aspects, the array of needles may comprise a plurality of needles with structural means for controlling skin penetration and fluid delivery to the skin. In some other aspects, the array of needles may further comprise a manufactured random or structured nanotopography on each needle. The needle or needle array may be attached to a larger drug delivery apparatus comprising fluidic delivery rate controls, adhesives for attaching to the skin, fluidic pumps, and the like. If desired, the rate of delivery of the agent may be variably controlled by the pressure-generating means. Desired delivery rates as described herein to the epidermis may be initiated by driving the one or more agents described herein with the application of pressure or other driving means, including pumps, syringes, pens, elastomer membranes, gas pressure, piezoelectric, electromotive, electromagnetic or osmotic pumping, or use of rate control membranes or combinations thereof. Particular exemplary structures and devices comprising a means for controllably delivering one or more agents to the epidermis are described in US20110270221, US20120187814, US20130144217, US20130144257, US20130150822, US20130158505, US20130165861, US 20140343532, US 20150360018, US 20150367117, and US 20160106965, each of which is incorporated by reference herein in their entirety.

In some embodiments described herein, the delivery device may comprise a needle array in the form of a patch. In some aspects, the array of needles are able to penetrate a most superficial layer of the stratum corneum and initially deliver one or more agents as described herein to at least a portion or all of the non-viable epidermis, at least a portion of or all of the viable epidermis, and/or at least a portion of the viable dermis of a subject and subsequently to one or more tumors. These needles may further comprise nanotopography on the surface of the needle in a random or organized pattern. In some aspects, the nanotopography pattern may demonstrate fractal geometry.

Figure 3:
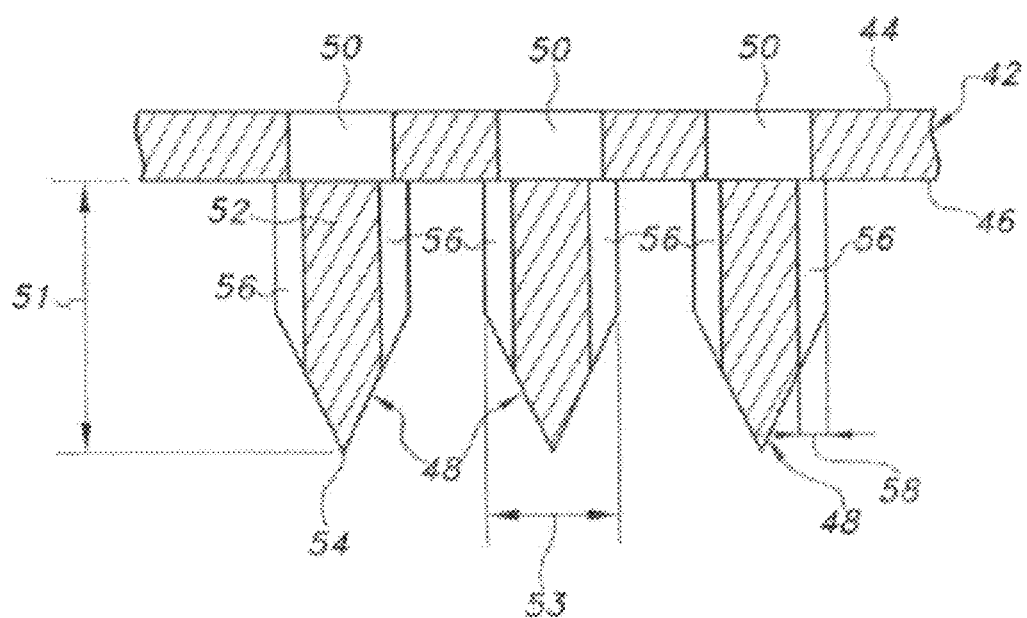
FIG. 3. Schematic of an exemplary delivery structure for administering an active agent to the skin.
Figure 4:
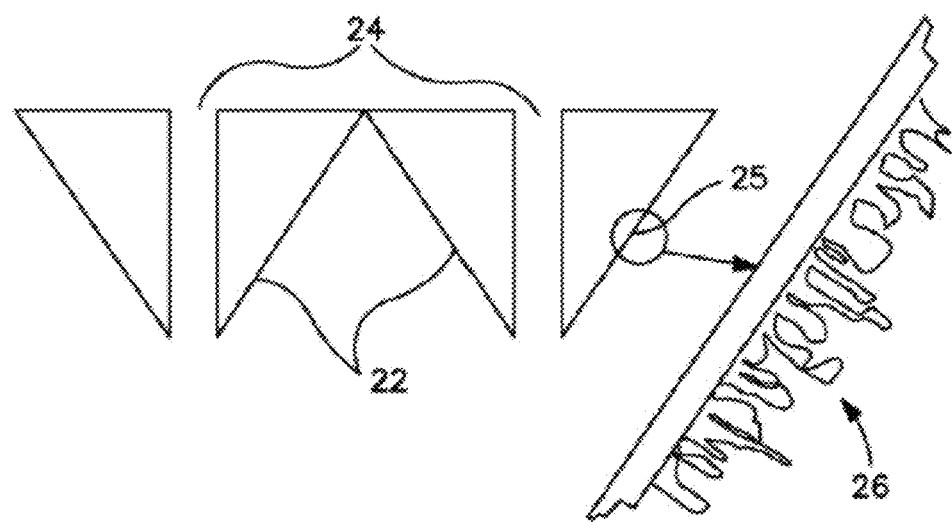
FIG. 4. Schematic of an exemplary delivery structure having a nanotopography surface for administering an active agent to the skin.

Exemplary and non-limiting devices and structures for delivering one or more agents to the skin are shown in FIGS. 3 and 4. As shown in FIG. 3, the needle assembly as illustrated may include a support 42 having a top surface 44 and a bottom surface 46 and defining a plurality of apertures 50 between the top and bottom surfaces 44, 46. In addition, the needle assembly may also include a plurality of needles 48 extending outwardly from the bottom surface 46. As described above, each needle 48 may define one or more channel(s) 56 in fluid communication with the apertures 50. As such, the active formulation in a liquid carrier as described herein contained within the suitable reservoir may be directed from the top surface 44 of the support 42 through the apertures 50 and into the needles 48 for subsequent delivery to the user's skin. The methods described herein, provide for the delivery of one or more agents to the layer of the skin and ultimately to a susceptible lymphatic capillary plexus and/or a blood capillary plexus.

The needles described above my further comprise nanotopography as described herein. FIG. 4 schematically illustrates the ends of two representative needles 22. In this particular embodiment, the needles 22 define a central exit lumen 24 that may be used for delivery of an agent via each needle 22 of a needle array as described herein. In some other embodiments, the needles may have multiple exit lumens for the delivery of an agent via the needle. The surface 25 of the needle 22 may define a nanotopography area 26. In this particular embodiment, the nanotopography 26 defines a random pattern on the surface 25 of the needle 22; however, in some other embodiments the nanotopography may be structured or in a partially structured/unstructured manner.

In some embodiments described herein, delivery devices comprising a needle array with nanotopography as described herein function as a permeability enhancer and may increase the delivery of one or more agents through the epidermis. As described herein, this delivery may occur through modulating transcellular transport mechanisms (e.g., active or passive mechanisms) or through paracellular permeation. Without being bound by any theory, the nanostructured or nanotopography surface may increase the permeability of one or more layers of the viable epidermis, including the epidermal basement membrane by modifying cell/cell tight junctions allowing for paracellular or modifying cellular active transport pathways (e.g., transcellular transport) allowing for diffusion or movement and/or active transport of an administered agent through the viable epidermis and into the underlying viable dermis. This effect may be due to modulation of gene expression of the cell/cell tight junction proteins. As previously mentioned, tight junctions are found within the viable skin and in particular the viable epidermis. The opening of the tight junctions may provide a paracellular route for improved delivery of any agent, such as those that have previously been blocked from delivery through the skin.

In some embodiments described herein, delivery devices comprising a needle array with nanotopograhy modulate the gene nucleic acid expression of a cell/cell contact gene of one or more viable epithelial cell types (e.g., a viable epidermal, dermal skin cell, blood capillary cell or lymphatic capillary cell). In some aspects, the nucleic acid gene expression of one or more cell/cell contact proteins is increased. In some aspects, the nucleic acid gene expression of one or more cell/cell contact proteins is decreased. Any method for measuring gene expression levels may be used including but not limited to, PCR, RT-PCR, qRT-PCR, microarrays, northern blotting, RNA Seq, and the like.

Interaction between individual cells and structures of the nanotopography may increase the permeability of an epithelial tissue (e.g., the epidermis) and induce the passage of an agent through a barrier cell and encourage transcellular transport. For instance, interaction with keratinocytes of the viable epidermis may encourage the partitioning of an agent into the keratinocytes (e.g., transcellular transport), followed by diffusion through the cells and across the lipid bilayer again. In addition, interaction of the nanotopography structure and the corneocytes of the stratum corneum may induce changes within the barrier lipids or corneodesmosomes resulting in diffusion of the agent through the stratum corneum into the underlying viable epidermal layers. While an agent may cross a barrier according to paracellular and transcellular routes, the predominant transport path may vary depending upon the nature of the agent.

In some embodiments described herein, delivery devices comprising a needle array with nanotopography modulate the protein expression of a cell/cell contact gene of one or more viable epithelial cell types (e.g., a viable epidermal, dermal skin cell, blood capillary cell or lymphatic capillary cell). In some aspects, the protein expression of one or more cell/cell contact proteins is increased. In some aspects, the protein expression of one or more cell/cell contact proteins is decreased. Any method for measuring protein expression levels may be used including but not limited to western blotting, tissue imaging (e.g., fluorescent or chemiluminescent imaging), mass spectrometry, and the like.

In some embodiments described herein, the device may interact with one or more components of the epithelial tissue to increase porosity of the tissue making it susceptible to paracellular and/or transcellular transport mechanisms. Epithelial tissue is one of the primary tissue types of the body. Epithelial tissues that may be rendered more porous may include both simple and stratified epithelium, including both keratinized epithelium and transitional epithelium. In addition, epithelial tissue encompassed herein may include any cell types of an epithelial layer including, without limitation, keratinocytes, endothelial cells, lymphatic endothelial cells, squamous cells, columnar cells, cuboidal cells and pseudostratified cells. Any method for measuring porosity may be used including but not limited to any epithelial permeability assay. For example, a whole mount permeability assay may be used to measure epithelial (e.g., skin) porosity or barrier function in vivo. In one embodiment, a whole mount permeability assay uses 5-bromo-4-chloro-3-indolyl-β, D-galactopyranoside (X-Gal). Unfixed, untreated samples are rinsed with phosphate buffered saline (PBS) and briefly dried. Samples are immersed in a standard X-Gal reaction mixture with the pH adjusted to 4.5. After incubating at 37° C. for 8-10 hrs, the samples are washed with PBS for 1-2 minutes and analyzed. In one embodiment, a whole mount permeability assay uses a histological dye such as, but not limited to, toluidine blue or hematoxylin. Unfixed, untreated samples are incubated for 1-5 minutes in methanol and rinsed in PBS. Samples are incubated in 0.5% hematoxylin or 0.1% toluidine blue then embedded in agarose for analysis. In one embodiment, sample analysis is performed by photographing the prepared samples and evaluated based on the degree of dye penetration. Other methods as are known in the art may also be used. See, for example, Indra and Leid., *Methods Mol Biol.*, (763) 73-81 (2012), which is incorporated by reference herein for its teachings thereof.

In some embodiments described herein, the structural changes induced by the presence of a nanotopography surface on a barrier cell are temporary and reversible. It was surprisingly found that using nanostructured nanotopography surfaces results in a temporary and completely reversible increase in the porosity of epithelial tissues by changing junctional stability and dynamics, which without being bound by any theory, may result in a temporary increase in the paracellular and transcellular transport of an administered agent through the epidermis and into the viable dermis. Thus, in some aspects, the increase in permeability of the epidermis or an epithelial tissue elicited by the nanotopography, such as promotion of paracellular or transcellular diffusion or movement of one or more agents, returns to a normal physiological state that was present before contacting the epithelial tissue with a nanotopography following the removal of the nanotopography. In this way, the normal barrier function of the barrier cell(s) (e.g., epidermal cell(s)) is restored and no further diffusion or movement of molecules occurs beyond the normal physiological diffusion or movement of molecules within the tissue of a subject.

These reversible structural changes induced by the nanotopography may function to limit secondary skin infections, absorption of harmful toxins, and limit irritation of the dermis. Also the progressive reversal of epidermal permeability from the top layer of the epidermis to the basal layer may promote the downward movement of one or more agents through the epidermis and into the dermis and prevent back flow or back diffusion of the one or more agents back into the epidermis.

In some alternative embodiments, the methods for delivering one or more agents to the skin comprises not only a needle, microneedle, or nanoneedle-based injection means, but other delivery methods, such as needle-less or needle-free ballistic injection of fluids, iontophoresis techniques, and direct deposition of fluid, solids, or other dosing forms into the epidermis of the skin.

In some embodiments described herein, are methods for applying a device having at least 2 or more delivery structures to the surface of the skin a subject for the treatment of a disease or disorder described herein. In some aspects, the device is applied to an area of the subject's skin, wherein the location of the skin on the body is dense in lymphatic capillaries and/or blood capillaries. Multiple devices may be applied to one or more locations of the skin having a dense network of lymphatic capillaries. In some aspects, 1, 2, 3, 4, 5, or more devices may be applied. These devices may be applied spatially separate or in close proximity or juxtaposed with one another. Exemplary and non-limiting locations dense with lymphatics comprise the palmar surfaces of the hands, the scrotum, the plantar surfaces of the feet and the lower abdomen.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the specified embodiments. All of the various embodiments, aspects, and options disclosed herein can be combined in all variations. The scope of the compositions, formulations, methods, and processes described herein include all actual or potential combinations of embodiments, aspects, options, examples, and preferences herein described. All patents and publications cited herein are incorporated by reference herein for the specific teachings thereof.

Example 1. Diagram of the Skin

The overall structure of the skin including the dermis and epidermis is illustrated in FIG. 1. The dermis is composed of a myriad of tissue types, and in general, exhibits an overall thickness ranging from about 500 µm to about 4,000 µm. The lymphatic and blood capillaries are found often found together as illustrated or they can be present as separate entities. As illustrated, the blood and lymphatic capillaries are often located within the upper portions of the dermis (e.g., near the epidermal dermal or epidermal basement membrane) within a portion of the papillary dermis. Larger vessels are generally found within the lower reticular dermis (e.g., a blood vessel as shown). Other tissue types important to dermal function include the larger arteries, arterioles, sweat gland ducts, sebaceous glands, nerve corpuscles, connective tissues and extra cellular matricis, smooth muscle, and hair follicles. Below the reticular dermis lies the subcutaneous tissue layer, which is composed largely of fat tissue and generally is void of any lymphatic or blood vasculature.

Figure 2:
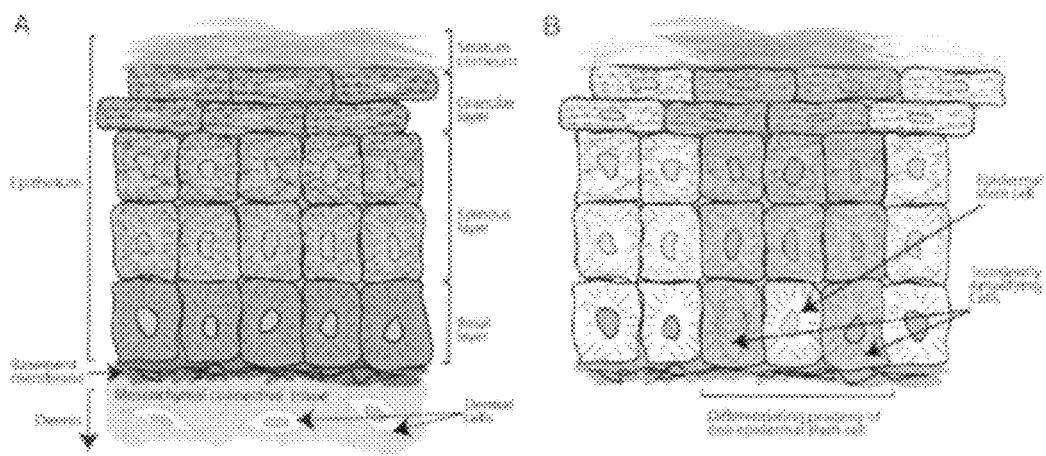
FIG. 2. Schematic of the epidermis illustrating the layers of the epidermis.

As illustrated in FIG. 2A, the epithelial skin layer is formed of four principal cellular layers lacking the many other tissue types of the dermis (e.g., blood and lymphatic capillaries, etc.) with a general thickness ranging from about 20 µm to about 400 µm. As illustrated from top to bottom is the basement membrane followed by the basal layer or stratum germinativum, the squamous cell layer or the stratum spinosum (spinous layer), the granular cell layer or the stratum granulosum, and the cornified layer or the stratum corneum. The epidermis is principally non-mitotic with the stratum corneum comprising non-viable enucleated barrier providing cells; however, as illustrated in FIG. 2B the basal layer consists of symmetrically dividing stem cells and other transiently amplifying cells for the regeneration of the corneum.

Example 2. Depth of Penetration into the Skin

Figure 6:
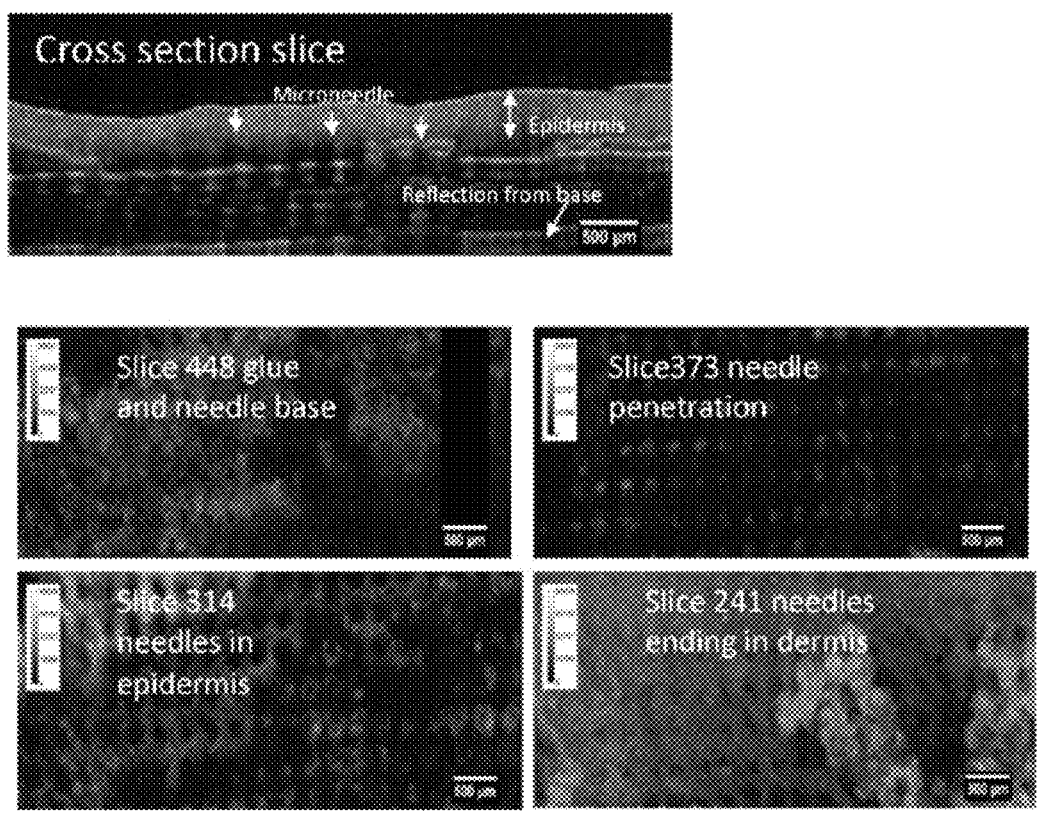
FIG. 6. Optical coherence tomography (OCT) imaging of the skin following penetration of the skin with a needle array.

An array of needles was fabricated on a patch and was used to estimate the average range of depth of delivering of an agent within the skin of adult guinea pigs. As shown in FIG. 5, methylene blue dye was administered to an average depth of about 92 µm demonstrating a range of depth distributions of about 5 µm to about 200 µm (a Gaussian distribution of depths). As shown in FIG. 6, the structure and depth in the skin may be estimated by using optical coherence tomography techniques. The structure of the skin after applying an array of needles can be visualized by looking at individual horizontal slices of the skin.

Example 3. Modulation of Epidermal Tight Junction Proteins

Figures 7A, 7B, 7C:
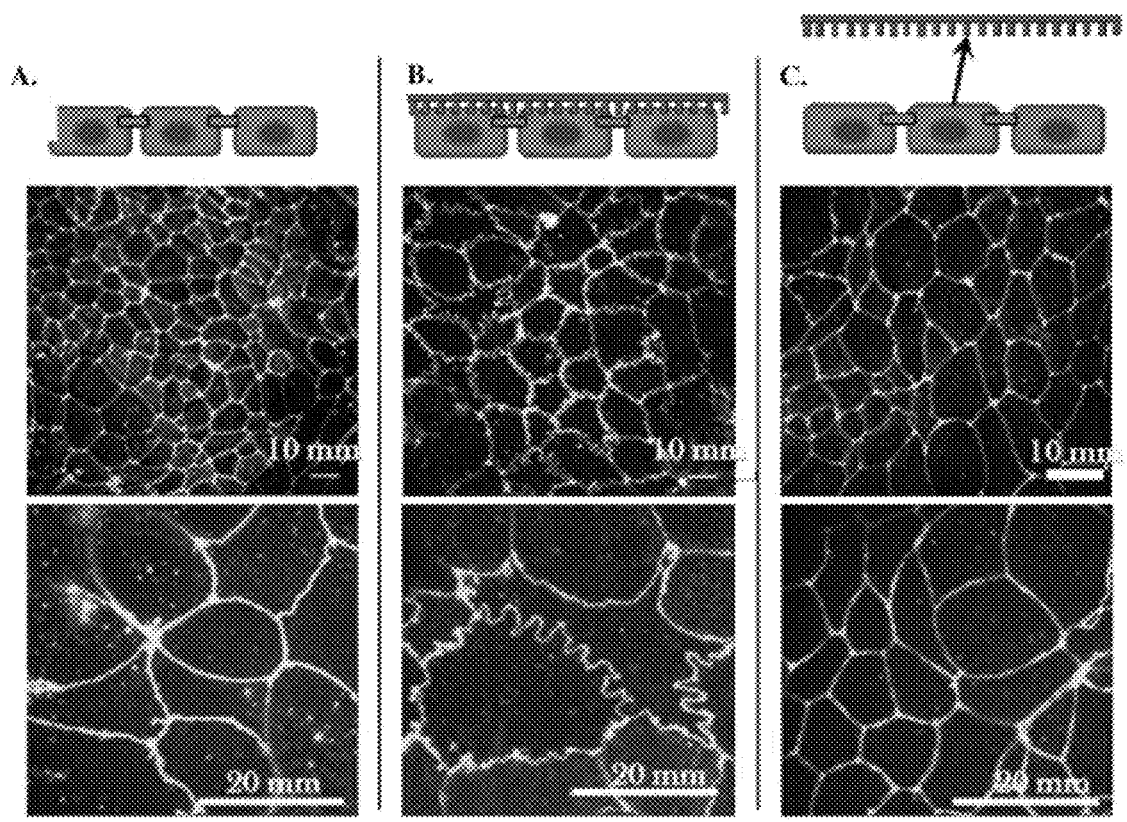
FIG. 7. Modulation of tight junction proteins by nanotopography containing needles in Caco-2 epithelial cells.

An array of needles having a nanotopography surface was fabricated on a patch and tested on an in vitro mono layer of Caco-2 epithelial cells. As shown in FIG. 7A, the ZO-1 tight junction protein shows a normal staining pattern. However, when an array of needles having a nanotopography surface is placed within proximity of Caco-2 cells, a disrupted staining pattern can be visualized. This ruffled pattern indicates junction remodeling in the areas of where the nanotopography was located (FIG. 7B). When the array of needles having a nanotopography is removed, the staining pattern returns to normal, indicating a spatial and temporal effect on tight junction proteins, such as ZO-1 (FIG. 7C).

Example 4. Better Delivery of Trastuzumab (Herceptin®) to Tumors in Vivo

Figure 8:
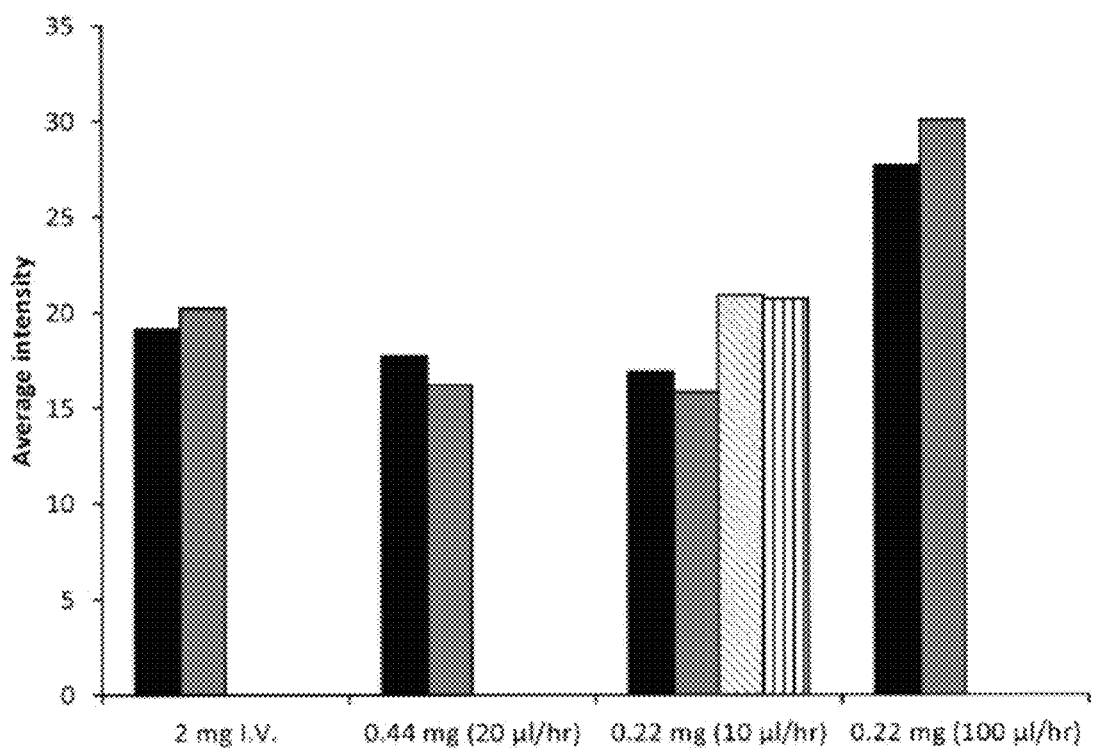
FIG. 8. Targeted delivery of an anti-cancer drug (trastuzumab) to tumors in vivo following delivery to the skin of rats.
Figure 9A:
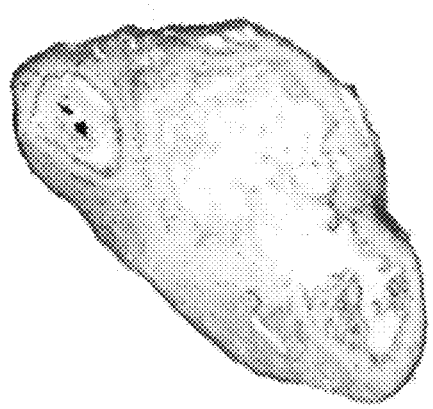
FIGS. 9A and 9B Representative tumors following delivery of an anti-cancer drug (trastuzumab) to the skin of rats.
Figure 9B:
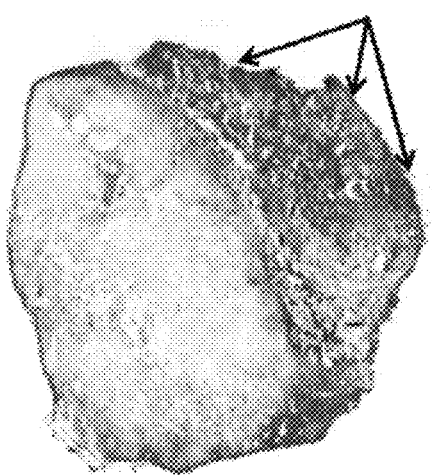

The ability to deliver trastuzumab (an anti-cancer drug) to tumors via administration to the skin was tested in a mouse xenograft tumor model. The HER-2 positive JIMT-1 human breast cancer cell line was used to generate xenograft tumors in mice. An array of needles having a nanotopography surface was fabricated on a patch and applied to the dorsal surface of mice presenting with tumors. These mice were then administered different amounts of trastuzumab at different administration rates to the skin and the concentration of trastuzumab in tumors was assessed. As shown in FIG. 8, administration of 0.22 mg of trastuzumab at a rate of 100 µl/hr yielded higher concentrations of trastuzumab in JIMT-1 tumors compared to approximately a 10 fold greater dosage of trastuzumab administered intravenously (2 mg i.v.). Trastuzumab administered to the skin demonstrated a greater or equivalent efficacy in treating tumors as evidenced by large areas of tumor necrosis (black arrows pointing to sections of necrotic tissue) when compared to even higher doses of trastuzumab administered intravenously (FIG. 9A-B).

Example 5. Better Delivery of Drugs to Tumors in Vitro

Figures 10A, 10B, 10C, 10D:
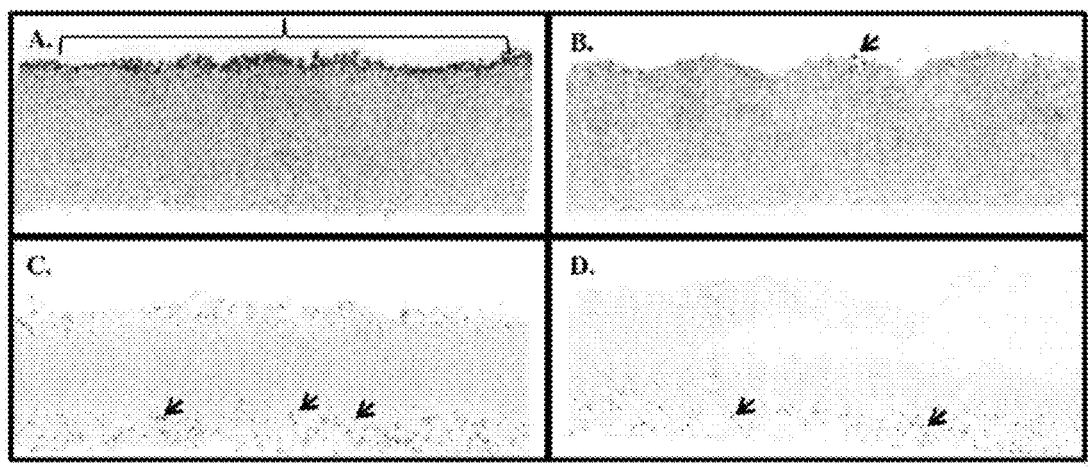
FIGS. 10A and 10B. Distribution of drugs delivered to in vitro grown tumors using an array of needles or by drug supplemented tissue culture media.
FIGS. 10C and 10D. Drug delivery method effects on proliferation of tumor tissue cells grown in vitro following drug delivery using an array of needles or by drug supplemented tissue culture media.

The efficiency of directly delivering drugs within in vitro grown tumors using an array of needles having a nanotopography surface was tested. Tumor tissues were grown in vitro and administered an anti-cancer drug by either adding drug to the tissue culture media or administering with an array of needles. The distribution of the drug was assessed by cryosectioning and subsequent tissue visualization (FIGS. 10A and 10B). The effects on cancer cell proliferation were measured using standard proliferation assay staining techniques following drug delivery. As shown in FIG. 10A, simple addition of the drug to the culture media led to little drug absorption throughout the tumor with the majority being retained within cells at the surface layer (as shown by the bracket). In contrast, as shown in FIG. 10B, administration of the drug to the tumor with an array of needles demonstrated higher levels of distribution throughout the tumor tissue slice with little being retained at the surface (as shown by black arrow head). Drugs that were only supplemented with the tissue culture media had a reduced anti-proliferative effect (FIG. 10C) compared to direct administration using an array of needles (FIG. 10D; examples of proliferating cells indicated by arrow heads).

Figure 11:
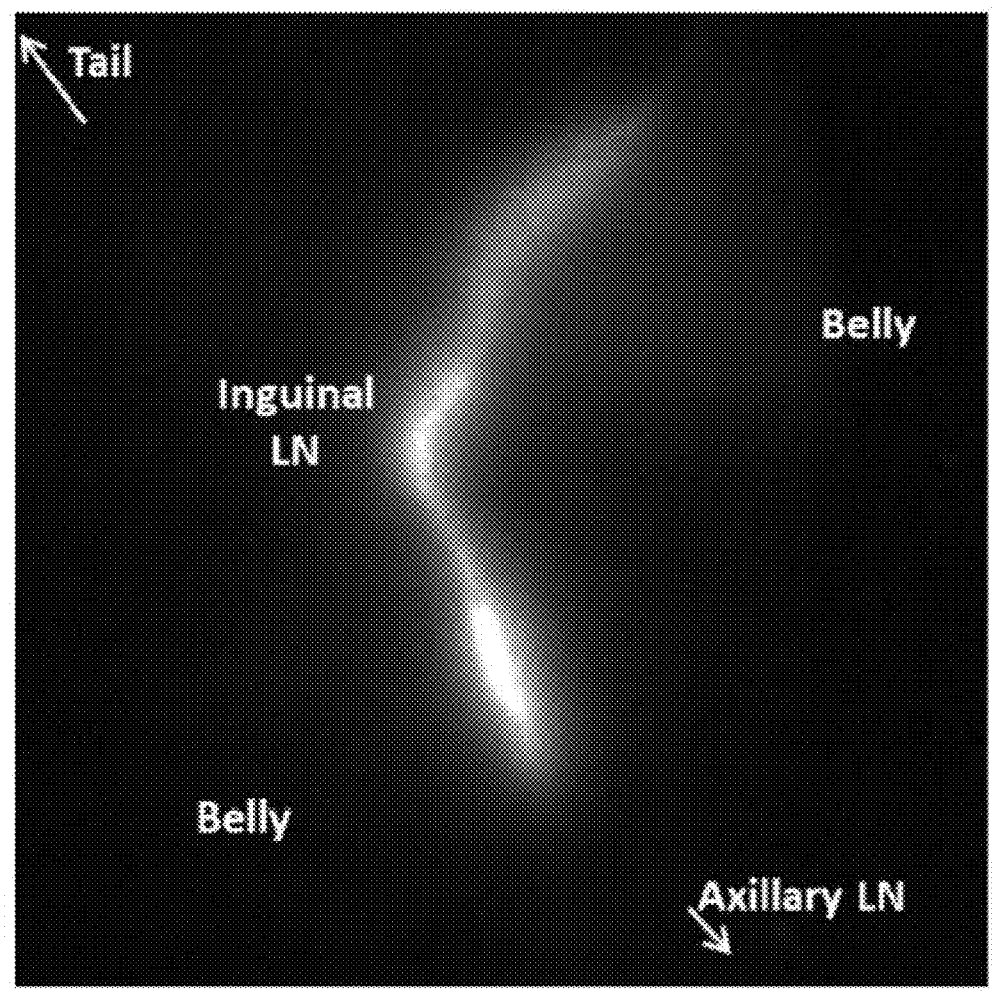
FIG. 11. Imaging of fluorescently tagged drug (Etanercept) administered to the skin showing delivery directly to the lymphatic vasculature and lymph node tissues.
Figure 12:
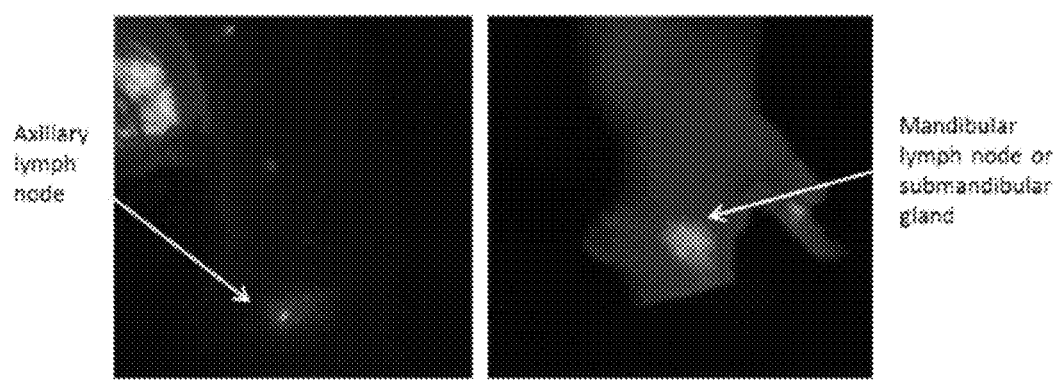
FIG. 12. Imaging of fluorescently tagged drug (Etanercept) administered to the skin showing delivery to the axillary and mandibular lymph nodes.

Example 6. In Vivo Imaging of Lymphatic Delivery of Etanercept (Enbrel®—an Anti-Inflammatory Drug) to the Lymphatic Vasculature and Biodistribution in Rats The ability to deliver the protein therapeutic Etanercept directly to the lymphatic system via administration to the skin was tested. Etanercept was fluorescently tagged for in vivo visualization using near infrared light as previous described, see Sevick-Muraca et al., *J. Clin Invest.*, 124(3), 905-914 (2014), which is incorporated by reference herein for its teachings thereof. Etanercept was administered to the skin of rats by placing a delivery device comprising an array of needles dorsally on the rats. As shown in FIG. 11 and FIG. 12, administration of etanercept to the skin resulted in uptake by the lymphatic vasculature and subsequent distribution to primary and secondary lymph node tissues.

Figure 13:
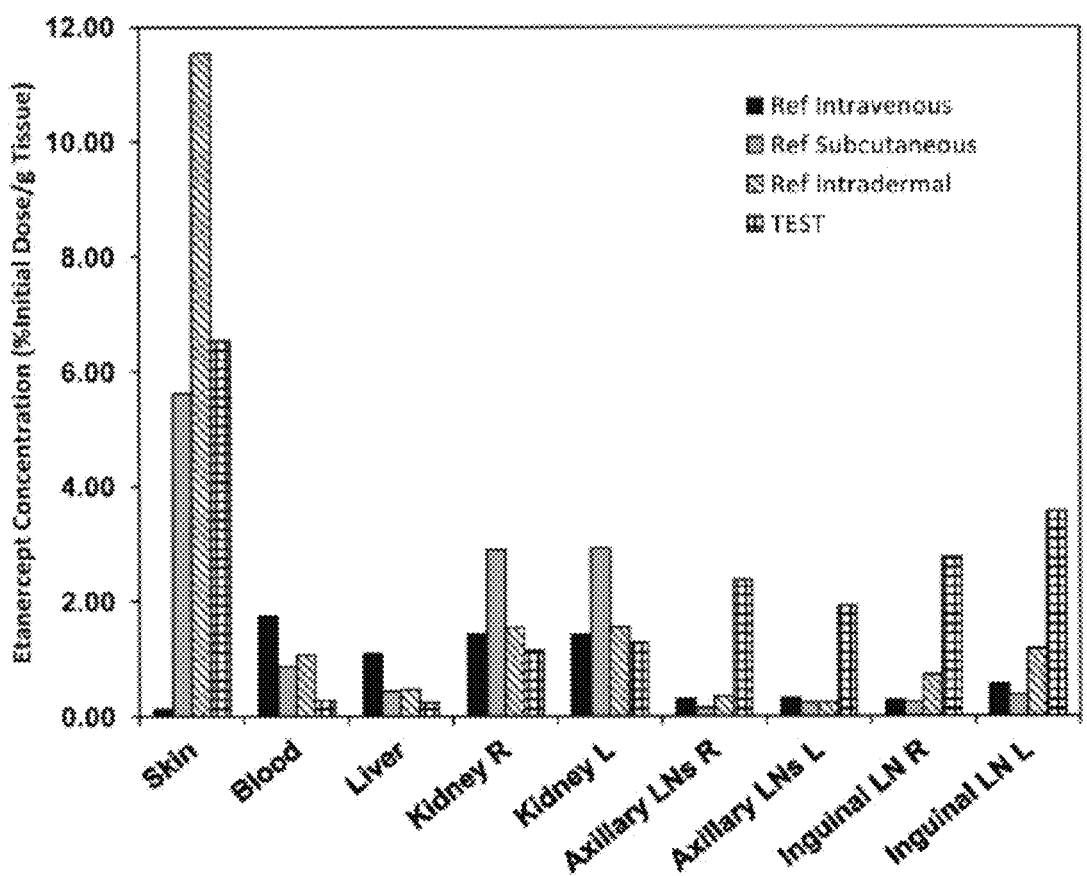
FIG. 13. Biodistribution for Etanercept following delivery to the skin using the methods of the present invention illustrating increased delivery to the lymph nodes compared to traditional delivery methods.

The biodistribution of etanercept across multiple tissues types following delivery was investigated. Accordingly, delivering etanercept to the skin resulted in much higher levels within the axillary and inguinal lymph nodes when compared to traditional i.v., s.c., or i.d. methods (FIG. 13).

Figure 14:
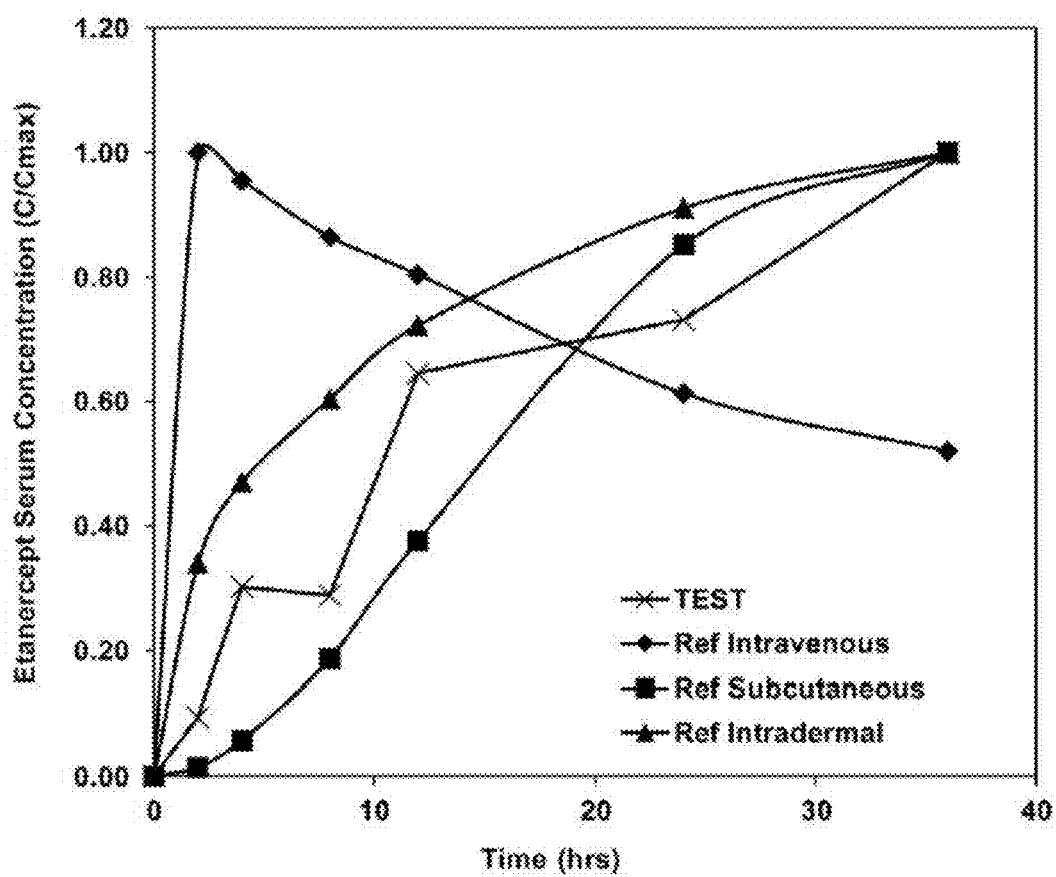
FIG. 14. Blood serum absorption rate of a drug (Etanercept) following delivery to the skin showing that the blood serum absorption rate is similar to traditional reference delivery methods.

Example 7. Rate of Blood Serum Absorption of Etanercept after Delivery to the Skin As shown in FIG. 14, the blood serum absorption rate of etaoercept following administration to the skin is approximately the same as i.v., s.c., or i.d. methods.

What is claimed is:
1. A method of delivering one or more agents to one or more susceptible tumors of a subject, the method comprising:
(a) applying one or more delivery devices having between 2 and 50,000 delivery structures to one or more sites of a skin of a subject comprising blood vasculature or lymphatic vasculature, wherein the one or more delivery devices contacts one or more layers of epidermis with one or more reversible permeability enhancers comprising a chemical, physical or electrical permeability enhancer that induces a reversible increase in permeability of one or more barrier cells of the epidermis to at least the one or more agents;
(b) administering a total liquid dosage in between 2 and 50,000 sub-doses of the one or more agents at a controlled administration flow rate of from about 0.01 µl/hr to about 100 µl/hr per each of the delivery structures at a total combined controlled administration flow rate of about 0.02 µl/hr/cm2 to about 50,000 µl/hr/cm2 based on a total surface area of the one or more delivery devices that is in contact with a skin of the subject,
wherein each sub-dose of the one or more agents is independently administered, in an administering step, to a plurality of independent depths ranging from about 1 µm to about 500 µm beyond a most superficial surface layer of the epidermis of the subject, but still within the epidermis of the subject exhibiting a Gaussian distribution of delivery depths within the epidermis prior to any subsequent diffusion or movement of the one or more agents within the epidermis; and
wherein following the administering step, the one or more agents moves or diffuses deeper through the epidermis through a basal layer of the epidermis and into at least a portion of underlying viable dermis to achieve an uptake of a portion of the one or more agents by one or more susceptible blood capillary plexus or lymphatic capillary plexus; and
wherein following administration, the permeability of the one or more barrier cells returns to a state prior to contact of the epidermis with the one or more reversible permeability enhancers.
2. The method according to claim 1, wherein the total liquid dosage of the one or more agents is administered to a plurality of depths within the epidermis consisting only of one or more viable epidermal layers and not a non-viable epidermal layer.

3. The method according to claim 1, wherein an average of the plurality of independent depths exhibits a combined average sub-dose delivery depth within the epidermis of about 70 μm to about 175 μm beyond the most superficial surface layer of the epidermis.

4. The method according to claim 1, wherein the delivery device comprises an array comprising between 2 and 50,000 of the delivery structures in fluid communication with the one or more agents in a liquid carrier vehicle,
   wherein the delivery device comprises a means for controlling the administration flow rate including at least one component selected from the group consisting of a pump, a fluid delivery rate controller, a syringe, a pen, an elastomer membrane, or any combination thereof;
   wherein the delivery structures comprise a means for penetrating at least a most superficial layer of the epidermis; and
   wherein the one or more agents in the liquid carrier vehicle is delivered by the delivery structures to the plurality of independent depths within a viable epidermis of the subject, thereby administering the between 2 and 50,000 sub-doses of the one or more agents.

5. The method according to claim 1 wherein the delivery structures comprise needles.

6. The method according to claim 1, wherein the one or more agents is delivered to a tissue volume of the epidermis encompassing the one or more agents prior to any subsequent diffusion or movement of the one or more agents within the epidermis of about 0.7 mm³ to about 2,500 mm³.

7. The method according to claim 1, wherein the one or more permeability enhancers is one or more chemical, physical, or electrical permeability enhancers.

8. The method according to claim 1, wherein administration of one or more agents achieves a dermal interstitial fluid pressure in the portion of underlying viable dermis beneath a site of administration of about 1 mmHg to about 15 mmHg.

9. The method according to claim 1, wherein the one or more agents circulate through the one or more susceptible blood capillary plexus and into or within proximity to one or more susceptible tumors.

10. The method according to claim 1, wherein the one or more agents comprise a bioactive agent.

11. The method according to claim 10 wherein the bioactive agent is useful for treating, retarding progression of, delaying onset of, prophylaxis of, amelioration of or reducing symptoms of a disease comprising the one or more tumors.

12. The method of claim 10, wherein a greater concentration of the one or more bioactive agents is delivered to the one or more tumors compared to intravenous, intradermal, or subcutaneous delivery of the one or more bioactive agents.

13. The method according to claim 1, wherein a concentration of the one or more agents within one or more susceptible tumors is about 1.25 fold to about 50 fold more than intravenous, intradermal, or subcutaneous delivery of the one or more agents.

14. The method according to claim 1, wherein after administration and uptake, the one or more agents circulates through the blood vasculature or lymphatic vasculature to one or more tumors.

* * * * *